(12) United States Patent
Liu

(10) Patent No.: US 10,603,352 B2
(45) Date of Patent: Mar. 31, 2020

(54) FORMULATIONS OF HEPALATIDE

(71) Applicant: SHANGHAI HEP PHARMACEUTICAL CO., LTD., Shanghai (CN)

(72) Inventor: Hongli Liu, Shanghai (CN)

(73) Assignee: Shanghai HEP Pharmaceutical Co., Ltd., Shanghai (CN)

(*) Notice: Subject to any disclaimer, the term of this patent is extended or adjusted under 35 U.S.C. 154(b) by 0 days.

(21) Appl. No.: 14/901,249

(22) PCT Filed: Jun. 24, 2014

(86) PCT No.: PCT/CN2014/080568
§ 371 (c)(1),
(2) Date: Dec. 28, 2015

(87) PCT Pub. No.: WO2015/000371
PCT Pub. Date: Jan. 8, 2015

(65) Prior Publication Data
US 2017/0112898 A1 Apr. 27, 2017

(30) Foreign Application Priority Data
Jul. 1, 2013 (CN) .......................... 2013 1 0273122

(51) Int. Cl.
A61K 38/16 (2006.01)
A61K 47/26 (2006.01)
A61K 9/19 (2006.01)
A61K 9/00 (2006.01)
A61K 47/02 (2006.01)
C12N 7/00 (2006.01)

(52) U.S. Cl.
CPC .......... A61K 38/162 (2013.01); A61K 9/0019 (2013.01); A61K 9/19 (2013.01); A61K 38/16 (2013.01); A61K 47/02 (2013.01); A61K 47/26 (2013.01); C12N 7/00 (2013.01); C12N 2730/10122 (2013.01); C12N 2730/10132 (2013.01)

(58) Field of Classification Search
None
See application file for complete search history.

(56) References Cited

U.S. PATENT DOCUMENTS

| | | | |
|---|---|---|---|
| 6,204,036 B1 | 3/2001 | Metzner et al. | |
| 6,838,084 B1 | 1/2005 | Jochmus et al. | |
| 2006/0002918 A1 | 1/2006 | Jiang et al. | |
| 2015/0030629 A1* | 1/2015 | Kraan | A61K 47/02 424/217.1 |

FOREIGN PATENT DOCUMENTS

| | | | |
|---|---|---|---|
| CN | 1733798 A | | 2/2006 |
| CN | 101199851 A | | 6/2008 |
| CN | 102241744 A | | 11/2011 |
| CN | 102241744 | * | 4/2015 |
| JP | H04330280 A | | 11/1992 |
| JP | H05345729 A | | 12/1993 |
| WO | 8909610 A1 | | 10/1989 |
| WO | 2004071536 A1 | | 8/2004 |
| WO | 2008/121615 A2 | | 10/2008 |
| WO | 2010045415 A2 | | 4/2010 |
| WO | WO2011140984 | * | 11/2011 |

OTHER PUBLICATIONS

Zhou, et al., "Pharmaceutics", Southeast University Press, First Edition, Mar. 31, 2007, pp. 119, 120, 149 [No English Language Translation Available].
PCT International Search Report, PCT/CN2014/080568, dated Sep. 29, 2014, 4 pages.
Supplementary European Search Report issued in European Patent Application No. EP 14 82 0112, dated Nov. 17, 2016, 16 pages.
Response to the Supplementary European Search Report issued in European Patent Application No. EP 14 82 0112, dated Jun. 13, 2017, 7 pages.
Masato Okada, Kaoru Miyazaki edit, Matchless Biotechnical Series, "Protein Experiment Note" revised version, First Volume, Separation Refining, Kabishiki-kaisha Yodo-sha, Mar. 20, 2002, pp. 17-22.
Japan Patent Office, Notification of Reasons for Refusal, Application No. 2016-522216, dated Jan. 23, 2018, 10 pages.
First Office Action issued in corresponding Chinese Patent Application No. 201310273122.3, dated Feb. 14, 2018, 13 pages.
Kuroda S, Otaka S, Miyazaki T, Nakao M, Fujisawa Y., "Hepatitis B virus envelope L protein particles. Synthesis and assembly in *Saccharomyces cerevisiae*, purification and characterization," J Biol Chem. vol. 267, No. 3, Jan. 25, 1992, pp. 1953-1961.

* cited by examiner

Primary Examiner — Maury A Audet
(74) Attorney, Agent, or Firm — Quarles & Brady LLP

(57) ABSTRACT

The present disclosure provides a drug formulation for hepalatide, comprising hepalatide and a buffer salt, and containing or not containing an osmotic regulator and/or an excipient.

18 Claims, 5 Drawing Sheets

Specification includes a Sequence Listing.

```
SEQUENCE LISTING

<160> NUMBER OF SEQ ID NOS: 2

<210> SEQ ID NO 1
<211> LENGTH: 47
<212> TYPE: PRT
<213> ORGANISM: Artificial Sequence
<220> FEATURE:
<223> OTHER INFORMATION: synthetic

<400> SEQUENCE: 1

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 2
<211> LENGTH: 10
<212> TYPE: PRT
<213> ORGANISM: Artificial Sequence
<220> FEATURE:
<223> OTHER INFORMATION: synthetic

<400> SEQUENCE: 2
```

-continued

```
Asp His Trp Pro Glu Ala Asn Gln Val Gly
1               5                   10
```

FORMULATIONS OF HEPALATIDE

CROSS-REFERENCE TO RELATED APPLICATIONS

The present application represents the national stage entry of PCT International Patent Application No. PCT/CN2014/080568 filed on Jun. 24, 2014, which claims priority of Chinese patent application No. 201310273122.3 filed on Jul. 1, 2013, the disclosures of which are incorporated herein by reference for all purposes.

TECHNICAL FIELD

The present disclosure relates to drug formulations of hepalatide and methods for preparing the same.

TECHNICAL BACKGROUND

1. Hepalatide

Hepalatide is a polypeptide disclosed in Chinese application No. 201010174788.X, the amino acid of which is set forth in SEQ ID NO: 1 of the Chinese application and also in SEQ ID NO: 1 of the subject application. The N terminus of the polypeptide is modified by myristic acid and the C terminus is modified by amidation. Hepalatide can effectively block the infection of liver cells by hepatitis B virus.

The amino acid sequence of Hepalatide is derived from the HBV large surface protein, which was known to assemble to form particles of 23-120 nm in vitro (Kuroda S, Otaka S, Miyazaki T, Nakao M, Fujisawa Y., Hepatitis B virus envelope L protein particles. Synthesis and assembly in *Saccharomyces cerevisiae*, purification and characterization, J Biol Chem. 1992 Jan. 25; 267(3):1953-61).

2. Current Status on Research of Formulation of Polypeptide Drug

Polypeptide drug consists of amino acids which connect in series. Different combinations of amino acids make the polypeptide to have unpredictable spatial structure and physical and chemical properties. Important pharmaceutical properties of the polypeptide, such as solubility, stability, ionization and pH, etc., are more easily to be affected by the surrounding environmental solution than the small molecular drug. In the meantime, there are significantly different specific conditions and requirements on clinical use of different polypeptide drugs, and strict requirements on the drug formulation by the in vivo environment. As a result, the results on studying formulation of polypeptide drug are difficult to be predicted and dosage form and prescription for a specific polypeptide drug have to be explored through prescription screen. Hepalatide is a polypeptide drug newly developed by the inventor, thus currently there are no published reports about study on formulation of Hepalatide.

SUMMARY

The present disclosure relates to a formulation of Hepalatide, which is formulated by water and comprises hepalatide and a buffer salt, with or without an osmotic regulator and/or an excipient. The concentration of hepalatide may be in a range of from 0.1 mg/ml to 50 mg/ml. The buffer salt may be phosphate or carbonate in a concentration of 0.001M to 0.5M. Preferred buffer salt is a phosphate buffer salt, which may have a concentration of 0.001M to 0.5M and a $Na_2HPO_4:NaH_2PO_4$ molar ratio of from 0:100 to 100:0. Osmotic regulator may be glucose, or NaCl, or $MgCl_2$, or $CaCl_2$, or any combination thereof, which may have a concentration of from 0 mM to 500 mM. In a specific embodiment, the osmotic regulator is NaCl in a concentration of from 0 mM to 500 mM. The excipient may be mannitol, dextran, sorbitol, lactose, polyethylene glycol, or any combination thereof, with a concentration of 0% to 20%. In a specific embodiment, the excipient is mannitol in a concentration of 0% to 20%.

The present disclosure also relates to a sterile drug formulation prepared from the above drug formulation by sterilization or disinfection, a lyophilized drug formulation prepared from the above drug formulation or sterile drug formulation via lyopilization, and a liquid drug formulation prepared by dissolving and re-constructing with injectable water, and a use of these drug formulations in the manufacture of a medicament for treating a HBV infectious disease.

Specifically, the subject application provides a drug formulation for hepalatide, which is formulated by water and comprises (i) hepalatide and (ii) a buffer salt, with or without (iii) an osmotic regulator and/or an excipient. The hepalatide is a polypeptide with an amino acid sequence set forth in SEQ ID NO: 1 and modified by myristic acid at its N terminus and by amidation at its C terminus.

In one specific embodiment, the buffer salt is an acetic acid buffer salt, a citric acid buffer salt, a phosphate buffer salt or a carbonate buffer salt, preferably a phosphate buffer salt or a carbonate buffer salt.

In one specific embodiment, the buffer salt is a phosphate buffer salt or a carbonate buffer salt, preferably a phosphate buffer salt.

In one specific embodiment, the concentration of the buffer salt is from 0.001M to 0.5M, preferably from 0.01M to 0.1M, more preferably from 0.02M to 0.05M, more preferably 0.02M.

In one specific embodiment, the buffer salt is a phosphate buffer salt in a concentration of from 0.01M to 0.5M, preferably from 0.01M to 0.1M, more preferably from 0.02M to 0.05M, more preferably 0.02M.

In one specific embodiment, the molar ratio between $Na_2HPO_4:NaH_2PO_4$ is from 0:100 to 100:0, preferably from 70:30 to 95:5, more preferably from 81:19 to 95:5, more preferably 90:10.

In one specific embodiment, the osmotic regulator is glucose, NaCl, $MgCl_2$, $CaCl_2$ or any combination thereof. Alternatively, the drug formulation of the present disclosure does not contain an osmotic regulator. Alternatively, the drug formulation of the present disclosure does not contain glucose and/or sodium chloride. In other embodiments, the drug formulation of the present disclosure contains sodium chloride as an osmotic regulator.

In one specific embodiment, the concentration of the osmotic regulator is in the range from 0 mM to 500 mM, preferably from 50 mM to 200 mM, more preferably from 100 mM to 160 mM, more preferably from 116 mM to 154 mM, more preferably 116 mM.

In one specific embodiment, the osmotic regulator is sodium chloride in a concentration of from 0 mM to 500 mM, preferably from 50 mM to 200 mM, more preferably from 100 mM to 160 mM, more preferably from 116 mM to 154 mM, more preferably 116 mM.

In one specific embodiment, the excipient is mannitol, dextran, sorbitol, lactose, polyethylene glycol, or any combination thereof. Alternatively, the drug formulation of the present disclosure does not contain an excipient. In some embodiments, the drug formulation of the present disclosure contains mannitol or dextran as an excipient.

In one specific embodiment, the concentration of the excipient (w/v) is from 0% to 20%, preferably from 0.5% to 15%, more preferably from 1% to 5%, more preferably from 2% to 5%, more preferably from 2% to 4%, more preferably 4%.

In one specific embodiment, the excipient is mannitol in a concentration of from 0% to 20%, preferably from 0.5% to 15%, more preferably from 1% to 5%, more preferably from 2% to 5%, more preferably from 2% to 4%, more preferably 4%.

In one specific embodiment, the concentration of hepalatide is from 0.1 mg/ml to 50 mg/ml.

In one specific embodiment, the concentration of hepalatide is from 0.1 mg/ml to 8.0 mg/ml, preferably from 0.5 mg/ml to 5.0 mg/ml, more preferably from 1.0 mg/ml to 2.1 mg/ml, more preferably from 2.0 mg/ml to 2.1 mg/ml. Preferably, the concentration of hepalatide is 0.25 mg/ml, or 0.5 mg/ml, or 1.0 mg/ml, or 2.0 mg/ml, or 2.1 mg/ml, or 4.0 mg/ml, or 4.2 mg/ml, or 5.0 mg/ml, or 10.0 mg/ml, more preferably 2.0 mg/ml or 2.1 mg/ml, most preferably 2.1 mg/ml.

In one specific embodiment, the formulae of the liquid formulations are shown in the following tables (a), (b), (c), (d), (e), (f), (g), (h), and (i), preferably in (e) and (f) and more preferably in (e).

(a)

| pharmaceutical formulation | | Calculated in 1000 ml liquid formulation | |
|---|---|---|---|
| Component | Concentration | Component | content |
| Hepalatide | 8.0 mg/ml | Hepalatide | 8.0 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(b)

| pharmaceutical formulation | | Calculated in 1000 ml liquid formulation | |
|---|---|---|---|
| Component | Concentration | Component | content |
| Hepalatide | 5.0 mg/ml | Hepalatide | 5.0 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(c)

| pharmaceutical formulation | | Calculated in 1000 ml liquid formulation | |
|---|---|---|---|
| Component | Concentration | Component | content |
| Hepalatide | 4.2 mg/ml | Hepalatide | 4.2 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(d)

| pharmaceutical formulation | | Calculated in 1000 ml liquid formulation | |
|---|---|---|---|
| Component | Concentration | Component | content |
| Hepalatide | 4.0 mg/ml | Hepalatide | 4.0 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(e)

| pharmaceutical formulation | | Calculated in 1000 ml liquid formulation | |
|---|---|---|---|
| Component | Concentration | Component | content |
| Hepalatide | 2.1 mg/ml | Hepalatide | 2.1 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(f)

| pharmaceutical formulation | | Calculated in 1000 ml liquid formulation | |
|---|---|---|---|
| Component | Concentration | Component | content |
| Hepalatide | 2.0 mg/ml | Hepalatide | 2.0 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(g)

| pharmaceutical formulation | | Calculated in 1000 ml liquid formulation | |
|---|---|---|---|
| Component | Concentration | Component | content |
| Hepalatide | 1.0 mg/ml | Hepalatide | 1.0 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

(h)

| pharmaceutical formulation | | Calculated in 1000 ml liquid formulation | |
|---|---|---|---|
| Component | Concentration | Component | content |
| Hepalatide | 0.5 mg/ml | Hepalatide | 0.5 g |
| mannitol | 4% (w/v) | mannitol | 40 g |
| $Na_2HPO_4$ | 18 mM | $Na_2HPO_4 \cdot 12H_2O$ | 6.4465 g |
| $NaH_2PO_4$ | 2 mM | $NaH_2PO_4 \cdot 2H_2O$ | 0.3120 g |
| NaCl | 116 mM | NaCl | 6.7744 g |

| (i) pharmaceutical formulation | | Calculated in 1000 ml liquid formulation | |
|---|---|---|---|
| Component | Concentration | Component | content |
| Hepalatide | 0.25 mg/ml | Hepalatide | 0.25 g |
| mannitol | 4% (w/v) | mannitol | 40 g |
| Na$_2$HPO$_4$ | 18 mM | Na$_2$HPO$_4$·12H$_2$O | 6.4465 g |
| NaH$_2$PO$_4$ | 2 mM | NaH$_2$PO$_4$·2H$_2$O | 0.3120 g |
| NaCl | 116 mM | NaCl | 6.7744 g |

In one specific embodiment, the liquid drug formulation is prepared via sterilization or disinfection, preferably by filtration sterilization, to form a sterile drug formulation. More preferably, a filter membrane having a pore size less than 0.45 μm, further preferably a filter membrane having a pore size of 0.22 μm, is used to prepare the sterile drug formulation.

In one specific embodiment, the lyophilized drug formulation is prepared by lyophilization, preferably by lyophilizing a sterile liquid drug formulation.

In one specific embodiment, the drug formulation may be separately packaged in a sealed container. Preferably, glass bottles are used to separately package the drug formulation, then lyophilized and sealed by rubber plug and aluminum cover.

In one specific embodiment, each sealed container contains the drug formulation comprising hepalatide in an amount preferably in a range of from 0.25 mg to 8.0 mg, more preferably in a range of from 0.25 mg to 5.0 mg, more preferably in a range of from 1.0 mg to 2.1 mg, and more preferably in a range of from 2.0 mg to 2.1 mg. Preferably, each sealed container contains the drug formulation comprising hepalatide, in a fixed amount of 0.25 mg, or 0.5 mg, or 1.0 mg, or 2.0 mg, or 2.1 mg, or 4.0 mg, or 4.2 mg, or 5.0 mg, or 8.0 mg, preferably each sealed container contains hepalatide in an amount of 0.5 mg, or 1.0 mg, or 2.0 mg, or 2.1 mg, or 4.0 mg, or 4.2 mg, more preferably each sealed container contains hepalatide in an amount of 2.0 mg or 2.1 mg, further preferably each sealed container contains hepalatide in an amount of 2.1 mg.

In one specific embodiment, the lyophilized drug formulation may be re-dissolved with an aqueous solution, preferably with an injectable water, to form a liquid drug formulation.

The subject application includes use of the drug formulation of the present disclosure in the manufacture of a medicament for treating a HBV infectious disease.

The subject application also includes use of drug formulation of the present disclosure in the manufacture of a medicament for blocking infection to liver cell by HBV.

It should be understood that, generally the drug formulation of the present disclosure can be used in human being.

SPECIFIC MODE FOR CARRYING OUT THE INVENTION

Figure 1:
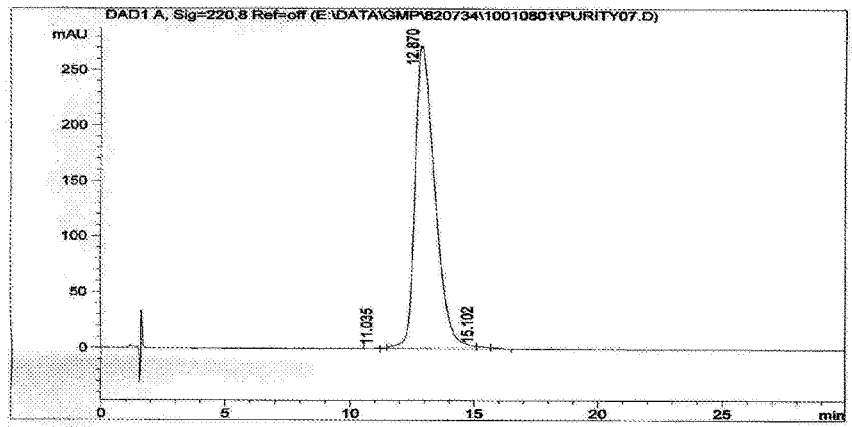
FIG. 1 shows the HPLC purity map of hepalatide.

As described above, the present disclosure provides a drug formulation of hepalatide, which is formulated by water and comprises hepalatide and a buffer salt, with or without an osmotic regulator and/or an excipient.

Hepalatide is a long peptide comprising 47 amino acids, with N terminus modified by myristic acid. Since myristic acid is a long chain fatty acid, its modification generally will make the product to have an improved hydrophobicity, resulting in that it is more difficult to formulate the drug. In the Examples, the solubility of hepalatide was detected and it was found that hepalatide was hardly soluble in water but was readily soluble in an organic solution, such as DMSO. Currently, formulating a hydrophobic drug is a common problem in the field of pharmacy. Generally, a hydrophobic drug is formulated by liposome, microsphere, or fat emulsion, etc. The process is complicated and tends to make the polypeptide drug to degrade. Therefore, it is crucial in the development of the pharmacology of hepalatide to prepare its water-soluble formulation. This can only be solved through practical exploration.

The isoelectric point (PI) of a polypeptide is very crucial for study of formulation. The pH value of a formulation should be far away from PI so as to ensure that the polypeptide is not ready to separate out or precipitate. In the Examples, PI of hepalatide was detected and found to be 4.5. Thus, hepalatide is an obviously acid polypeptide. In the Examples, investigation was carried out to improve the solubility of hepalatide in water was carried out by screening a suitable buffer salt system. Currently, medicinal buffers and their pH scopes include acetate (3.6-5.8), citrate (3.0-6.6), phosphate (5.8-8.0) and carbonate (9.1-10.8). After screening, it was found that hepalatide was hardly soluble in acetate buffer or citrate buffer and readily soluble in phosphate buffer and carbonate buffer. Thus, the phosphate buffer and carbonate buffer could be used as a buffer system for the drug formulation. In the Examples, stability of hepalatide in the buffer salt system was studied and it was found that phosphate was preferred, as a buffer system.

In the Examples, phosphate buffer was used to dissolve hepalatide for an in vivo pharmacodynamical study in an animal. With the study, the in vivo effective amount in an animal was determined and the dose for human use was calculated therefrom to 4.2 mg/60 kg. From the viewpoint of convenience for clinical use and dose regulation, preferred specification for the formulation is from 0.5 mg/bottle to 5 mg/bottle, more preferably from 1 mg/bottle to 5 mg/bottle, more preferably from 2 mg/bottle to 4 mg/bottle. For specification, 4.2 mg/bottle, or 4 mg/bottle, or 2.1 mg/bottle, or 2 mg/bottle, or 1 mg/bottle or 0.5 mg/bottle is preferred, 2.1 mg/bottle or 2 mg/bottle is more preferred, and most preferably, the specification for the formulation is 2.1 mg/bottle.

Although hepalatide can be well dissolved in phosphate buffer saline or carbonate buffer, it is surprising that the lyophilized drug formulation cannot be re-dissolved. The drug formulations of the present disclosure are to be used as injections for human body. Only when the drug concentration is 0.1 mg/ml the liquid formulation reconstructed therefrom could have a clarity that satisfies the requirement on clarity of an injection in the Chinese Pharmacopoeia. The amino acid of the drug, hepalatide, of the present disclosure is derived from the HBV large surface protein, which was known to assemble in vitro to form particles of 23-120 nm. Thus, the possible reason as to why the hepalatide drug formulation is difficult to be re-dissolved after lyophilization may be that the drug concentration is dramatically increased due to volatilization of water during lyophilization of the drug formulation, which results in formation of polymers. Un-dissolved agglutination and precipitation affects not only the effective concentration of the drug but also the physical and pharmaceutical properties of the formulation. Thus, there are strict requirements on re-dissolution property of the injection in the national Pharmacopoeia. A general strategy for overcoming this problem is to keep low concentration of the drug in the drug formulation. In the present disclosure, 0.1 mg/ml of drug concentration is used. According to the calculation of the pharmacodynamical dose, the dose for human use is 4.2 mg/dose. If the drug formulation is prepared according to the above drug concentration, then the dose volume for each dose of drug will be up to 42 ml. This will lead to not only larger syringe and package but also discomfort during administration and higher expense. More importantly, the drug formulation of the present disclosure is expected to be administered clinically by subcutaneous injection. The so large administration volume is a challenge for the clinical use. Another strategy for overcoming this problem is to introduce solute molecule to increase the hepalatide concentration of the drug formulation that could be re-dissolved after lyophilization. By screening the solute molecule of the conventional pharmaceutical osmotic regulator, and the excipient, it was found that merely introducing an osmotic regulator or excipient could only slightly increase the hepalatide concentration of the drug formulation that could be re-dissolved. In the study on the effect of a combination of osmotic regulator with excipient on re-dissolution after lyophilization of a drug formulation comprising 0.1 mg/ml hepalatide, it was found that mannitol-NaCl made the solubility of the lyophilized formulation becoming worse under that condition. But it was surprising that the mannitol-NaCl combination could improve the re-dissolution property after lyophilization of the drug formulation comprising a higher hepalatide concentration, such as 0.25-8.0 mg/ml. This is contrary to the common understanding. Combinations of other osmotic regulators and excipients fail to increase the hepalatide concentration in the drug formulation liquid that is used to prepare a lyophilized formulation to be re-dissolved, as done by the mannitol-NaCl combination.

In the Examples, the prescription of the formulation was screened for hepalatide in a phosphate buffer within the specification range of the formulation. In the meantime, the pH of the formulation should be near to the physiological range of 7.35-7.45 and the crystal osmotic pressure should be near to the isotonic level for sake of safe clinical use.

The lyophilized formulation has an advantage in stably storing the polypeptide drug. However, the drug, buffer system and excipient exhibit great effect on the lyophilization. Excipient was further screened, and lyophilization effect obtained under different concentrations of excipient was also screened in the Examples.

A complete and comprehensive screening was done in the Examples to screen the prescription of the formulation solution by using pH value, stability and excipient effect after lyophilization as indexes, to obtain the preferred components for the hepalatide formulation.

In the Examples, the lyophilized drug formulation was re-dissolved by an aqueous solution, which produces good re-dissolution effect.

In the Examples, the effect of the re-dissolved formulation solution in blocking in vivo and in vitro HBV infection was studied. It was found that the solution could effectively block HBV infection.

In the Examples, the stability of the lyophilized drug formulation was studied. It was found that the drug formulation exhibited an excellent stability and could fully satisfy requirements on production, transport, storage and clinical use.

The present invention will be further illustrated by making reference to the specific Examples. It should be understood that these Examples are merely for illustrating the present invention but not to limit the scope of the present invention. Experimental methods the specific conditions of which are not indicated in the following Examples will follow the conventional conditions as disclosed in Sambrook et al, Molecular Cloning: A Laboratory Manual, New York, Cold Spring Harbor Laboratory Press, 1989, and conditions disclosed in Chinese Pharmacopoeia, or follow the conditions recommended by the manufacturer.

EXAMPLE 1: PREPARATION OF HEPALATIDE

1. Experimental Method

Hepalatide was synthesized by a solid phase synthesis method according to the amino acid sequence of SEQ ID NO: 1. Specifically, amino acids from the C terminus (carboxyl terminus) to the N terminus (amino terminus) were linked to the solid resin support one by one until all of the amino acids of the polypeptide were linked and the polypeptide was modified by myristic acid. The target polypeptide was cleaved from the support and modified by amidation at the C terminus, thereby obtaining hepalatide of the present invention. The synthesized polypeptides were purified by preparative high performance liquid chromatography (HPLC). The major polypeptide component was effectively isolated from the impurities, such as polypeptide by product and truncated peptide, produced during preparation. The effluent liquid was fractionally collected and detected for purity respectively. The Trifluoroacetic acid in the effluent liquid containing the major component having qualified purity was converted to acetic acid and then the effluent liquid was freeze dried to obtain the finished hepalatide powder. The finished hepalatide product was subject to HPLC for detection of purity and to mass spectrum for detection of molecular weight. The N terminal sequence and the C terminal sequence of the prepared hepalatide were detected by N terminal degradation and mass spectrum. Detection conditions for HPLC purity included HP 1100 high performance liquid chromatograph and chromatographic work station software (Agilent, USA); mobile phase A: 0.1% TFA in $H_2O$; mobile phase B: 0.1% TFA in (80% ACN+20% $H_2O$); chromatographic column: Luna C18 (150 mm×4.6 mm, 5 μm, 100 Å); gradient: 54.0%-61.5% mobile phase B in 30 min; detection wavelength: 220 nm; column temperature: 30° C.; sample size: 20 μL; velocity of flow: 1.0 ml/min; loading concentration: 0.5 mg/ml. The percentage of the area of the major peak in the total area of peaks was calculated to obtain the purity of the drug.

2. Experimental Result

Figure 2:
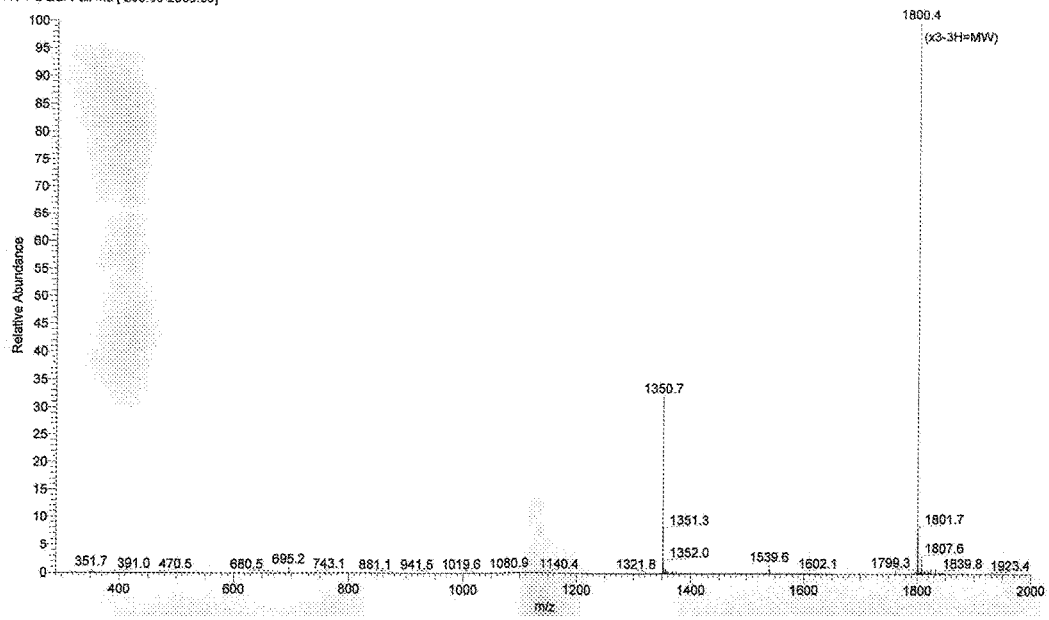
FIG. 2 shows the mass spectrometry map for the molecular weight of hepalatide.
Figure 3:
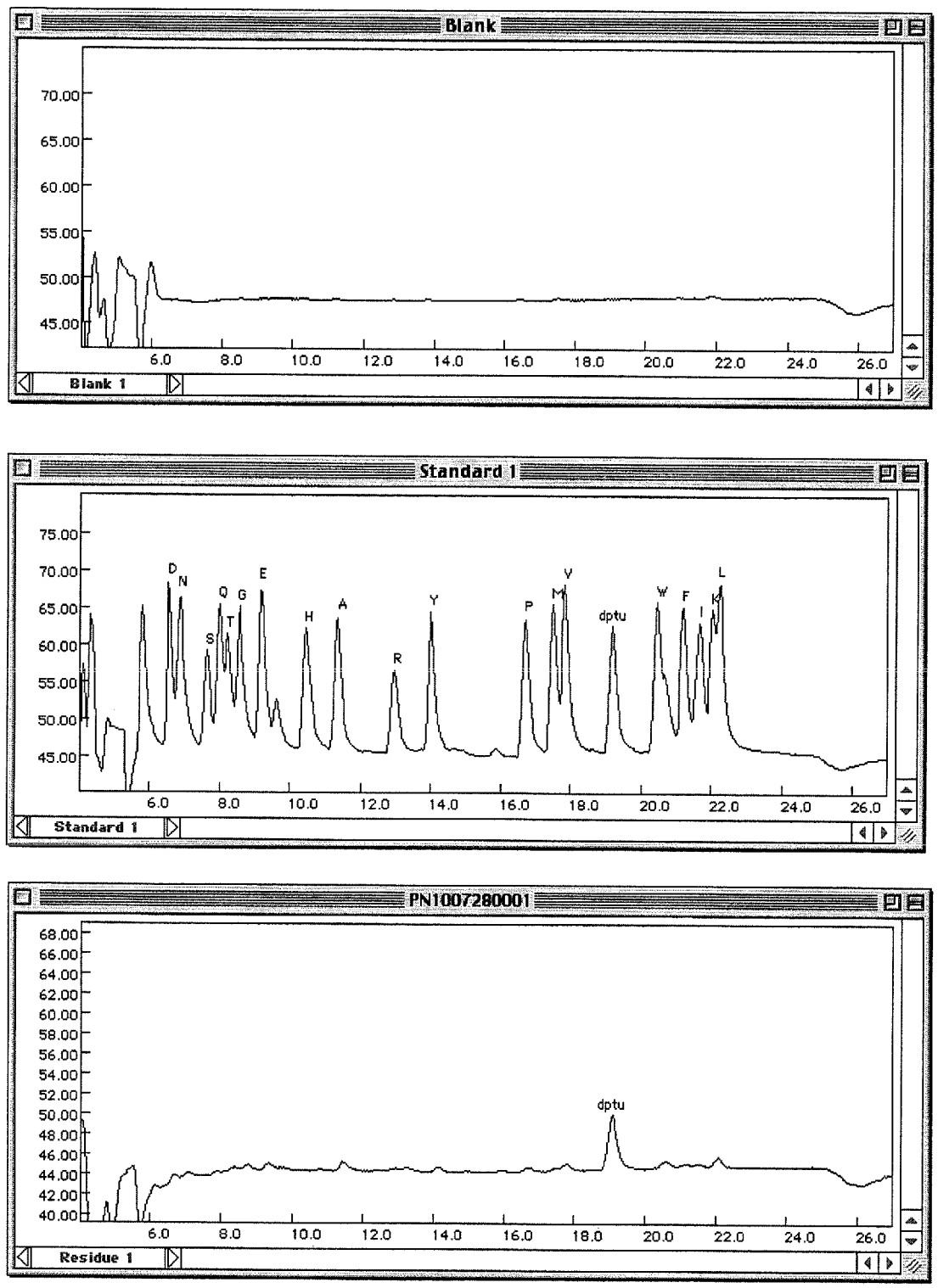
FIG. 3 shows sequencing map for the N terminus of hepalatide.
Figure 4:
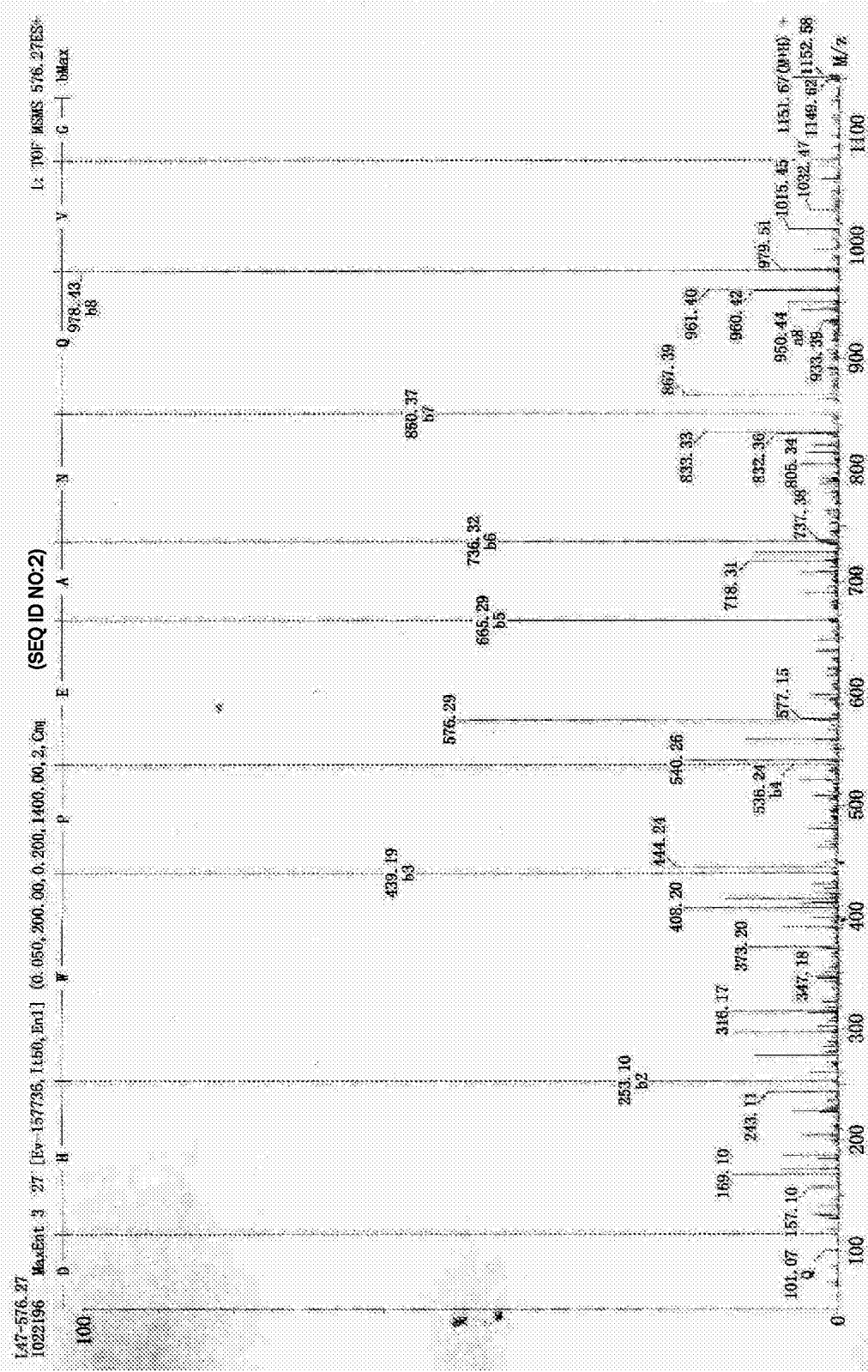
FIG. 4 shows sequencing map for the C terminus of hepalatide.

The HPLC purity of the prepared hepalatide was shown in FIG. 1, which was 99.4%. The molecular weight detected by mass spectrum was shown in FIG. 2. The theoretical molecular weight was 5398.8 Da and the found molecular weight was 5398.2 Da, which was consistent to the theoretical molecular weight. As shown in FIG. 3, the N terminus could not be degraded and thus no sequence was obtained, as evidenced by the N terminus sequencing. This is consistent to the modification of the N terminus of hepalatide by myristic acid. As shown in FIG. 4, the sequence at the C terminus was DHWPEANQVG (SEQ ID NO:2), with G being modified by amidation. This is consistent with the corresponding sequence in SEQ ID NO: 1.

EXAMPLE 2: DETECTION OF THE SOLUBILITY OF HEPALATIDE

1. Experimental Method

Study was conducted according to the general statement of Chinese Pharmacopoeia, 2010, Volume II. Specifically, a suitable amount of sample was weighed and added into a certain amount of solution at 25° C.±1° C. The solution was intensely vortexed for 30 seconds every 5 minutes. Dissolution situation was observed over 30 minutes. The polypeptide was considered dissolved if no visible solute particles were observed. Water, acetonitrile, DMSO and saline were used as solvents.

2. Result

TABLE 1

Results of solubility test

| Solvent | Solubility(mg/ml) |
| --- | --- |
| Water | 0 |
| acetonitrile | 0 |
| DMSO | >20 |
| saline | 0 |

EXAMPLE 3: DETECTION ON ISOELECTRIC POINT OF HEPALATIDE

1. Design of Test

Detection was carried out according to the "isoelectric focusing electrophoresis" for detecting the isoelectric point of a protein or peptide sample in the "electrophoresis" portion of the appendix of Chinese Pharmacopoeia, 2010, Volume II.

2. Test Materials pH3-10 amphoteric electrolyte: Amersham pharmacia biotech, USA;

Acrylamide: USB, USA;

Methylene-bisacrylamide: USB, USA;

Ammonium persulfate: USB, USA;

Gel support film: Bio-Rad, USA;

Model1 type Mini IEF cell: Bio-Rad, USA;

EPS601 type iontophoresis apparatus: Amersham pharmacia biotech, USA;

ARCUS-II type scanner: Agfa-Gevaert N.V. (AGFA)

3. Experimental Method a. Preparation of the solutions necessary for electrophoresis Solution A: 5.0 g acrylamide and 0.5 g methylene-bisacrylamide were weighed, dissolved by adding a suitable amount of water, diluted to 50 ml, filtered through a double-layer filter paper, and then stored in dark.

Solution B: 0.1 g ammonium persulfate was weighed and dissolved in 1 ml $H_2O$. Solution B is prepared immediately before use.

50% Glycerol: 50 g glycerol was weighed and dissolved in 80 ml $H_2O$. The final volume was set to 100 ml.

0.5 mol/L phosphoric acid solution (anode solution): 16.6 ml phosphoric acid was weighed and dissolved in 400 ml $H_2O$ and diluted to a final volume of 500 ml for spare use.

1 mol/L NaOH solution (cathode solution): 40 g NaOH was weighed and dissolved in 800 ml $H_2O$ and diluted to 1000 ml for spare use.

20% trichloroacetic acid (stationary liquid): 200 g trichloroacetic acid was weighed and dissolved in 80 ml $H_2O$ and diluted to 1000 ml for spare use.

Staining stock: 1.0 g Coomassie Brilliant Blue G-250 was weighed and dissolved in 20 ml water, as solution 1; 125 g ammonia sulfate was weighed and dissolved in 400 ml water, as solution 2; 20 g phosphoric acid was weighed as solution 3; Solution 3 was added into solution 1. After Coomassie Brilliant Blue G-250 was fully dissolved, the mixture of solutions 1 and 3 was mixed with solution 2. Water was added to 1 L and mixed uniformly to obtain the staining stock. Before use the staining stock should be adequately shaken up.

Staining working solution: 60 ml staining stock were mixed uniformly with 30 ml methanol, immediately before use.

b. Preparation of Gel film. A piece of glass sheet was provided and cleaned. And a piece of gel support film (Bio-rad) was provided. A small quantity of deionized water was sucked by a pipette and two drops of water were dropped onto each surface of the plastic film to identify its hydrophilic surface and hydrophobic surface. A thin layer of glue was uniformly applied on the hydrophobic surface and then the glass sheet was adhered to the hydrophobic surface of the plastic film. The bubbles were removed as much as possible by pressing. Then the sheet was placed for a short period to allow solidification. There were two plastic sheets with 10 mm width and 0.5 mm thickness at two sides of the film box prepared from gel. The hydrophilic surface of the plastic film on the glass sheet was placed downward to adhere closely to the plastic sheets at the two sides of one end of the film box, resulting in that the three surfaces of the glass plate adhered to the box wall while only one surface was open.

c. Preparation of Gel. 2.5 ml Solution A, 0.35 ml ampho-teric electrolyte with pH in the range of 3 to 10 (or amphoteric electrolyte having other pH ranges), 1.25 ml water and 0.5 ml 50% glycerol were mixed and degassed for 5-10 minutes. 25 µl Solution B and 6 µl N,N,N',N'-tetramethyl ethylenediamine were added. After gently mixing, the gel solution was slowly injected into the lower part of the glass plate through the open surface by a 1 ml pipette. The gel solution should be continuously flowed to avoid formation of bubble. When the gel was filled in the whole glass plate, injection was stopped. The glass plate was placed horizontally for 1 hour to allow the gel to sufficiently polymerize. After polymerization, the plastic film of the glass plate was connected to the gel. The gel could be removed from the film box and directly used, or could be packaged within a preservative film and stored in a refrigerator at 4° C. for spare use.

d. Pre-electrophoresis. The polymerized polyacrylamide gel was placed onto a cooling plate, during which liquid paraffin or kerosene was coated to avoid formation of bubble. Anode solution and cathode solution were used to moisten the electrode strips of the anode and cathode, respectively. Then the electrode strips were respectively placed onto the anode and the cathode. Electrodes were aligned to the center of the electrode strips and capped. Test was carried out under constant voltage. Pre-electrophoresis was done for 30 minutes at an initial voltage of 200V.

e. Loading. A plastic thin film (Bio-rad) with loading wells was covered on the surface of the gel to allow the thin film and the gel to fit together. For each well, 2 µl of protein sample were loaded. Marker from Mini-IEF was added in an appropriate well. 5-10 minutes were required after loading to allow the sample to enter into the gel and then the film with loading wells was removed.

f. Electrophoresis. Graphite electrodes in the electrophoretic box were cleaned and then moistened by water. The surface of the gel on which the samples were loaded was placed downward and the two ends of the gel were placed on the graphite electrodes. The electrophoresis chamber was covered by its lid and electrophoresis began. Ice bags were placed around the electrophoretic box to ensure that electrophoresis was done under low temperature. Under constant voltage, the voltage was firstly focused on 100V. 15 minutes later, the voltage was increased to 200V and focused for 15 minutes. Then the voltage was increased to 450V. 60 minutes later electrophoresis was finished. During the whole course electrophoresis was carried out at 4° C.

g. Staining and destaining. After electrophoresis was finished, the thin film was removed from the electrophoretic chamber and placed into a watch glass. The plastic film with gel was dipped in a fixative solution and then transferred to a staining solution for staining for 30 minutes. Then the film was transferred to a destaining solution for destaining to obtain a gel having a clear background. The whole course was carried out on an oscillator operated under low speed.

h. Photo scanning. The gel was placed in a gel electrophoresis scanner for scanning. The migration distance between the peptide and the isoelectric point standard was determined via a scan positioning method.

i. Judgment on result. Linear regression line was plotted by using the isoelectric point (pI) of various proteins in the isoelectric point standard reagent as a function of their respective migration distances. The migration distance of the sample was introduced into the linear regression equation to calculate its isoelectric point.

4. Method for Calculating Isoelectric Point

Linear regression line, L=aP+b, was plotted by using the isoelectric point (pI) of various proteins in the isoelectric point standard reagent as a function of their respective migration distances, wherein L is migration distance and P is isoelectric point. The migration distance (L) of sample L47 was introduced into the linear regression equation to calculate the isoelectric point of sample L47. The isoelectric point (P) of L47 was calculated according to the equation P=(L−b)/a.

5. Experimental Result

Figure 5:
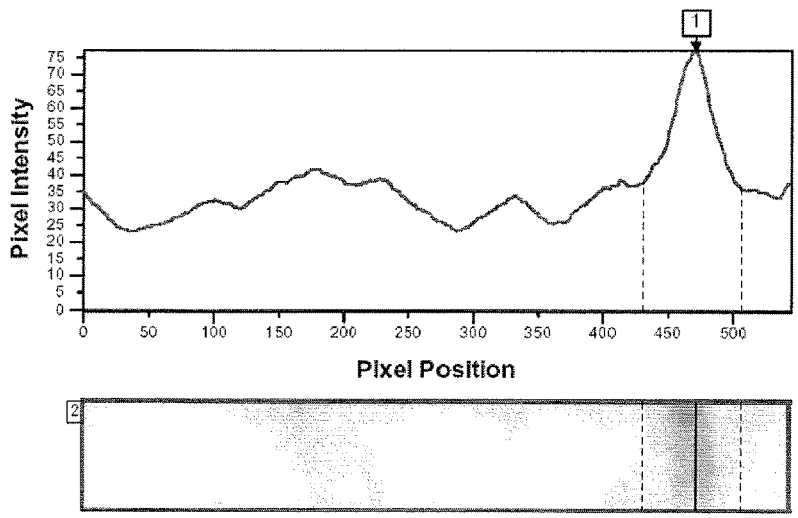
FIG. 5 shows the electrophorogram for isoelectric point and migration distance analysis for hepalatide.
Figure 6:
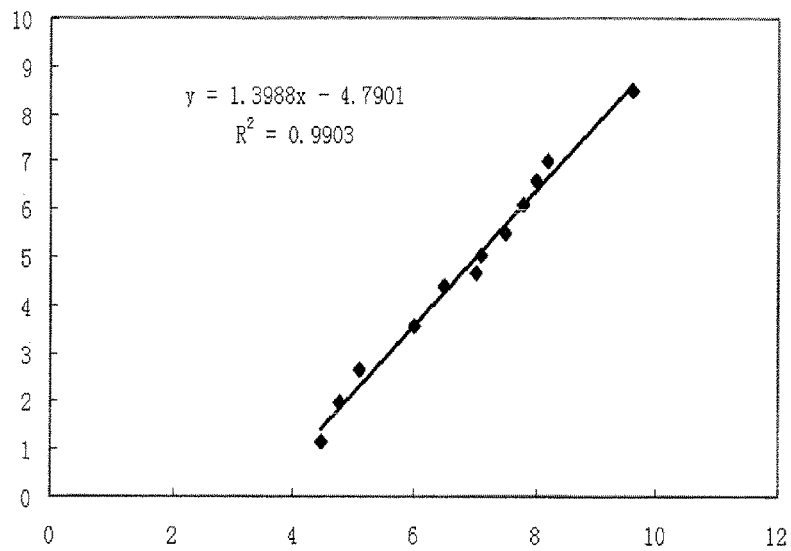
FIG. 6 shows migration distance in the isoelectric point detection-linear regression equation of isoelectric point for hepalatide.

The electrophoretic photos were shown in FIG. 5 and the isoelectric point-migration distance regression equation was shown in FIG. 6. The isoelectric point was calculated as follows:

| Migration distance-Isoelectric point Regression Equation | Correlation coefficient ($R^2$) | Migration distance | Isoelectric point (pI) |
|---|---|---|---|
| L = 1.3988P−4.7901 | 0.9903 | 1.50 | 4.50 |

EXAMPLE 4: PHARMACODYNAMICAL DOSE STUDY OF HEPALATIDE IN ANIMAL

1. Experimental Method

Systemic study on pharmacodynamics of drug for treating hepatitis B by using tree shrew as animal model was not reported presently. There was no successful case in which HBV chronic infection model was established in animal body with healthy immune system. And, since HBV merely infects human, chimpanzee and tree shrew, only tree shrew can be used as an animal infection model for evaluating pharmacodynamics of hepalatide. HBV infection in adult tree shrew is an acute and self-limiting course, with HBV being eliminated at the $6^{th}$ week. This system was used to evaluate the effectiveness of hepalatide in blocking HBV infection of hepatocyte in animal.

Fifty adult tree shrews were grouped randomly into 5 groups, which included PBS control group, high dose group (hepalatide, 2 mg/kg), middle dose group (0.4 mg/kg), low dose group (0.08 mg/kg) and HBIG blocking group (60 IU/kg). 1 ml HBV viral serum was intraperitoneally injected to infect tree threws. The hepalatide blocking groups were administered with different doses of hepalatide by subcutaneous injection at day 0, 1, 2, 3, 5, 7, 9, 11 and 13 after infection. For the HBIG blocking group, immunoglobulin HBIG was intramuscularly injected at the day the animal was infected and day 3 after infection. At day 4 before infection and day 9, 14, 21 and 42 after infection, sera were obtained from tree threws and HBsAg, HBeAg and HBV DNA titers and glutamic-pyruvic transaminase (ALT) in sera were detected. At day 21 after infection, liver tissue was obtained and subjected to pathological detection. Evaluation indexes for hepatitis B include serological index (HBsAg), virological index (copy number of HBV DNA) and biochemical index (ALT).

2. Experimental Result

Figure 7:
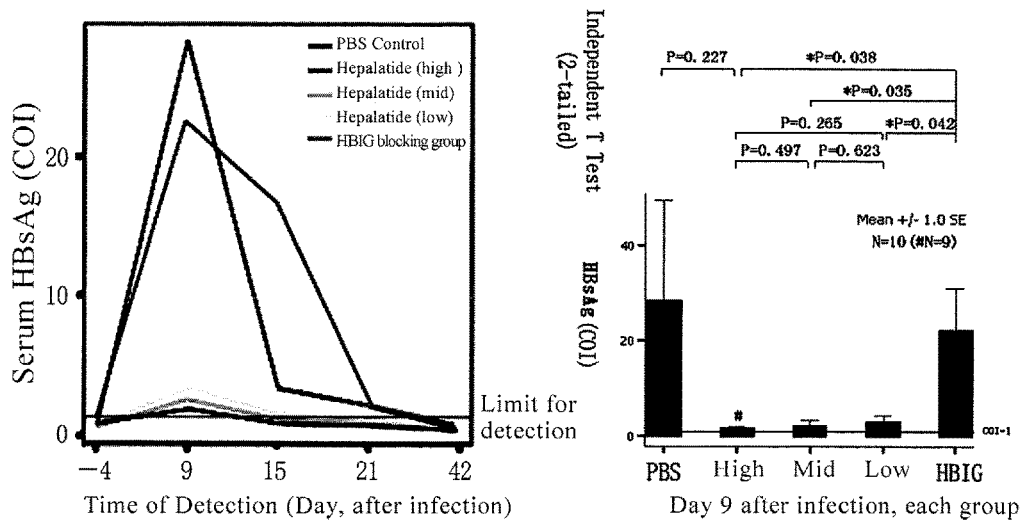
FIG. 7 shows a serological index (HBsAg) in an in vivo pharmacodynamic evaluation for hepalatide.
Figure 8:
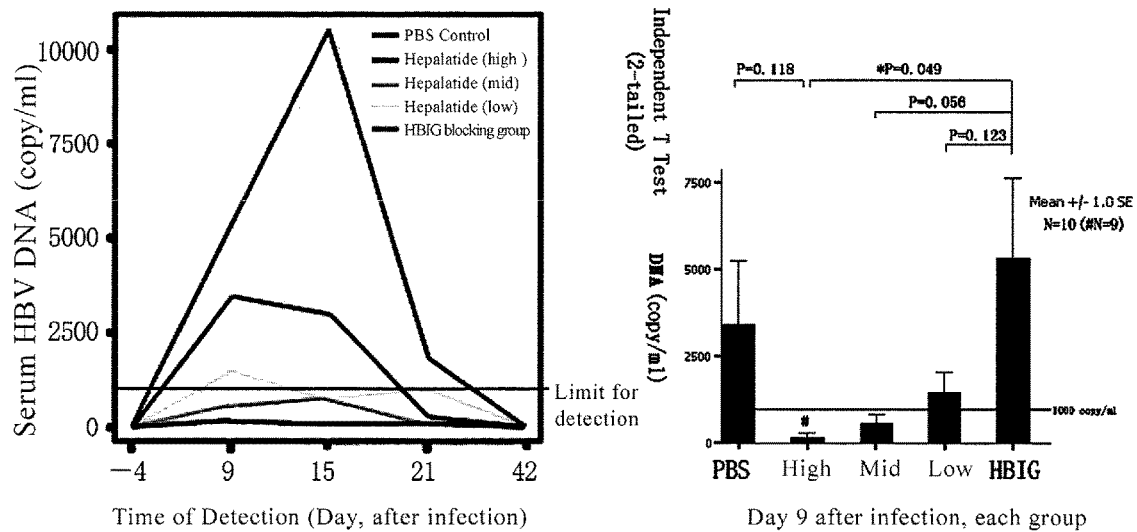
FIG. 8 shows a virological index (HBV DNA) in an in vivo pharmacodynamic evaluation for hepalatide.
Figure 9:
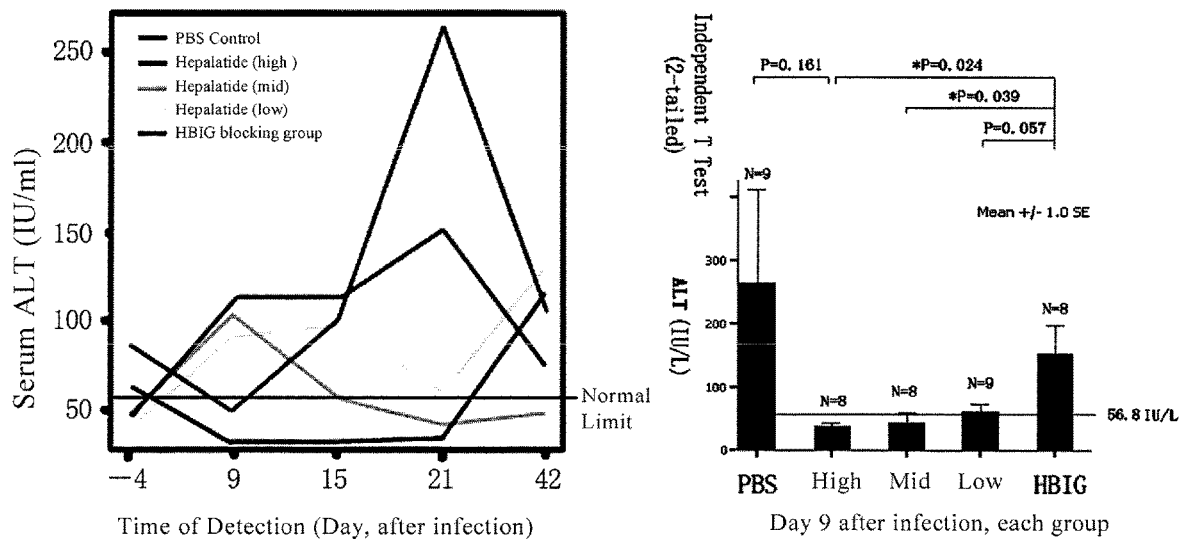
FIG. 9 shows a zymological index (ALT) in an in vivo pharmacodynamic evaluation for hepalatide.

As shown in FIGS. 7-9, according to the serological index (HBsAg), virological index (copy number of HBV DNA) and biochemical index (ALT), the dose of 0.4 mg/kg could effectively block in vivo HBV infection. Therefore, the pharmacodynamical dose in an animal was determined as 0.4 mg/kg. As calculated by body surface area, the effective dose for an adult human (60 kg) is 4.2 mg. From the viewpoint of convenience for clinical use and dose regulation, preferred specification for the formulation is from 0.5 mg/bottle to 5 mg/bottle, more preferably from 1 mg/bottle to 5 mg/bottle, more preferably from 2 mg/bottle to 4 mg/bottle. For specification, 4.2 mg/bottle, or 4 mg/bottle, or 2.1 mg/bottle, or 2 mg/bottle, or 1 mg/bottle or 0.5 mg/bottle is preferred, 2.1 mg/bottle or 2 mg/bottle is more preferred, and most preferably, the specification for the formulation is 2.1 mg/bottle.

EXAMPLE 5: SCREENING FOR BUFFER SYSTEM FOR HEPALATIDE FORMULATION

1. Experimental Method

Acetic acid-sodium acetate buffer (0.1M, pH=4.5), citric acid-sodium citrate buffer (0.1M, pH=4.8), disodium hydrogen phosphate-sodium dihydrogen phosphate buffer (0.1M, pH=7.4), sodium carbonate-sodium bicarbonate buffer (0.1M, pH=10.0) were prepared. Solubility of hepalatide in each buffer was determined by the method described in Example 2.

2. Experimental Result

Solubility of hepalatide in each buffer was shown in Table 2. Evaluated with the solubility, phosphate and carbonate were preferred buffers for the formulation solution.

TABLE 2

Solubility of Hepalatide in Buffer

| Buffer | Solubility (mg/ml) |
|---|---|
| Acetic acid buffer | ~0 |
| Citrate buffer | ~0 |
| Phosphate buffer | 10 |
| Carbonate buffer | >50 |

EXAMPLE 6: STABILITY ANALYSIS ON HEPALATIDE IN CARBONATE AND PHOSPHATE BUFFER

1. Experimental Method

Disodium hydrogen phosphate-sodium dihydrogen phosphate buffer (0.1M, pH=7.4) and sodium carbonate-sodium bicarbonate buffer (0.1M, pH=10.0) were prepared. A certain amount of hepalatide was weighed and dissolved respectively in the buffer to form solutions having a concentration of 2.1 mg/ml. The solutions were placed in an incubator for incubating at 37° C. The hepalatide purity was detected at the 0, 1, 2, 4, 8, 12, 16, and 24 hour by HPLC. The detection conditions were identical to those in Example 1.

2. Experimental Result

Stabilities of hepalatide in phosphate and carbonate buffer were shown in Table 3. Evaluated with the stability, phosphate was preferred as a buffer for the formulation solution.

TABLE 3

Purity of Hepalatide in Buffer (%)

| Time Point | Buffer | |
|---|---|---|
| (hour) | Phosphate buffer | Carbonate buffer |
| 0 | 99.4 | 99.4 |
| 1 | 99.4 | 99.1 |
| 2 | 99.3 | 98.8 |
| 4 | 99.4 | 97.5 |
| 8 | 99.2 | 95.3 |
| 12 | 99.0 | 92.7 |
| 16 | 98.7 | 90.5 |
| 24 | 98.5 | 85.2 |

EXAMPLE 7: LYOPHILIZATION AND RE-DISSOLUTION OF HEPALATIDE IN CARBONATE BUFFER AND Phosphate Buffer 1. Experimental Method Disodium hydrogen phosphate-sodium dihydrogen phosphate buffer (0.1M, pH=7.4) and sodium carbonate-sodium bicarbonate buffer (0.1M, pH=10.0) were prepared. A certain amount of hepalatide was weighed and dissolved respectively in the buffer to form drug formulation solutions having a concentration of 0, 0.1, 0.25, 0.5, 1.0, 2.1, 4.2, 8, or 10 mg/ml. The above formulation solutions were loaded into glass bottles in an amount of 1 ml/bottle. The bottles were placed into the cabinet of cryogenic freezing dryer (Supermodulyo, 0.4 m2, E-C Apparatus) for lyophilization according to the following procedure: pre-freezing at −40° C. for 4 hours; vacuumizing to 300 mT; setting a warming program of 1° C./min and raising the temperature to −20° C.; lyophilizing for 12 hours; setting a warming program of 1° C./min and raising the temperature to 30° C.; drying 4 hours; plugging and capping. The lyophilized drug formulation was re-dissolved with injectable water (1 ml/bottle). The re-dissolution of the lyophilized drug formulation was observed according to the method for detecting clarity described in appendix IX B, Chinese Pharmacopoeia, 2010, Volume II. The drug formulation of the subject example is an injection. According to the requirements in the Chinese Pharmacopoeia, the re-dissolved drug formulation should be clear. If it looks turbid, it should not be more turbid than the turbidity of No. 1 standard solution.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 4. Before lyophilization, hepalatide exhibited a good solubility in the drug formulation solution. The drug formulation was clear and not turbid. After lyophilization, it is surprisingly found that the lyophilized formulations prepared from the formulation solutions having a higher concentration of hepalatide are difficult to be re-dissolved after re-dissolving the lyophilized formulations. It is conjectured that the concentration of hepalatide in the formulation solution is gradually increased during lyophilization as water is continuously volatilized and polymer particles between the drug polypeptide were formed under high concentration, which are difficult to be re-dissolved. As a result, the re-constructed drug formulation looks turbid.

The experimental results show that after lyophilization and re-dissolution, the drug formulations containing hepalatide in a concentration of from 0 mg/ml to 0.1 mg/ml in a phosphate buffer exhibit clarity complying with requirements in the Chinese Pharmacopoeia, and the drug formulations containing hepalatide in a concentration of from 0 mg/ml to 0.25 mg/ml in a carbonate buffer exhibit clarity complying with requirements in the Chinese Pharmacopoeia. In the following Examples, other solutes, such as osmotic regulator or excipient, were added to investigate how to increase the concentration and amount of hepalatide in the lyophilized formulations that could be re-dissolved to make them to comply with related requirements in the Chinese Pharmacopoeia.

TABLE 4

Clarity of drug formulations after re-dissolved from lyophilized formulations having different hepalatide concentrations in formulation solutions

| Hepalatide Concentra- | Buffer | |
|---|---|---|
| tion(mg/ml) | Phosphate Buffer | Carbonate Buffer |
| 0 | Clear | Clear |
| 0.1 | Turbidity less than that of No. 1 standard solution | Clear |
| 0.25 | Turbidity greater than that of No. 1 standard solution | Turbidity less than that of No. 1 standard solution |

TABLE 4-continued

Clarity of drug formulations after re-dissolved from lyophilized formulations having different hepalatide concentrations in formulation solutions

| Hepalatide Concentration(mg/ml) | Buffer | |
|---|---|---|
| | Phosphate Buffer | Carbonate Buffer |
| 0.5 | Turbidity greater than that of No. 1 standard solution | Turbidity greater than that of No. 1 standard solution |
| 1.0 | Turbidity greater than that of No. 1 standard solution | Turbidity greater than that of No. 1 standard solution |
| 2.1 | Turbidity greater than that of No. 1 standard solution | Turbidity greater than that of No. 1 standard solution |
| 4.2 | Turbidity greater than that of No. 1 standard solution | Turbidity greater than that of No. 1 standard solution |
| 8.0 | Turbidity greater than that of No. 1 standard solution | Turbidity greater than that of No. 1 standard solution |
| 10.0 | Turbidity greater than that of No. 1 standard solution | Turbidity greater than that of No. 1 standard solution |

EXAMPLE 8: SCREEN OF OSMOTIC REGULATOR FOR FORMULATION SOLUTION (I)

1. Experimental Method $Na_2HPO_4$—$NaH_2PO_4$ buffer (0.1M, pH=7.4) was prepared, which contained 2.1 mg/ml hepalatide, and glucose, NaCl, $MgCl_2$ or $CaCl_2$ as an osmotic regulator in a final concentration of 5% (W/V), 0.9% (W/V), 100 mM and 100 mM, respectively. Formulation solution without osmotic regulator was also prepared. The formulation solutions were placed in an incubator for incubation at 37° C. The stability of hepalatide of the solutions was detected at each time point according to the method described in Example 1.

2. Experimental Result

Stability of hepalatide in the phosphate buffer with or without osmotic regulator is shown in Table 5. Evaluated with stability, the formulation solution preferably does not contain an osmotic regulator, or glucose, or NaCl, more preferably does not contain an osmotic regulator or NaCl, or further more preferably contains NaCl as an osmotic regulator.

TABLE 5

Purity (%) of hepalatide in drug formulation solutions of phosphate buffer containing an osmotic regulator

| Time Point (hour) | Osmotic Regulator | | | | |
|---|---|---|---|---|---|
| | Not contained | Glucose (5%) | NaCl (0.9%) | MgCl$_2$ (100 mM) | CaCl$_2$ (100 mM) |
| 0 | 99.4 | 99.4 | 99.4 | 99.4 | 99.4 |
| 4 | 99.4 | 99.4 | 99.4 | 98.5 | 98.0 |
| 8 | 99.2 | 99.2 | 99.3 | 97.9 | 95.1 |
| 12 | 99.0 | 99.0 | 99.1 | 97.4 | 92.8 |
| 16 | 98.7 | 98.7 | 98.9 | 97.2 | 90.7 |
| 24 | 98.5 | 98.6 | 98.7 | 97.1 | 85.3 |

EXAMPLE 9: SCREEN OF OSMOTIC REGULATOR FOR FORMULATION SOLUTION (II)

1. Experimental Method

Other solutes, such as osmotic regulator, were added to investigate how to improve the re-dissolution of the lyophilized formulation to allow increased concentration of hepalatide in the formulation solution. $Na_2HPO_4$—$NaH_2PO_4$ buffer (0.1M, pH=7.4) was prepared, which contained hepalatide in a concentration of 0, 0.1, 0.25, 0.5, 1.0, 2.1, 4.2, 8, or 10 mg/ml, and glucose, NaCl, $MgCl_2$ or $CaCl_2$ as an osmotic regulator in a final concentration of 5% (W/V), 0.9% (W/V), 100 mM and 100 mM, respectively. Formulation solution without osmotic regulator was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 6. As shown in the experimental results, introduction of a solute, such as an osmotic regulator such as glucose, NaCl or $MgCl_2$, exhibited no great effect on increase of the concentration of hepalatide in a drug formulation that could be re-dissolved after lyophilization, as their introduction merely increased the concentration of hepalatide from 0-0.1 mg/ml to 0-0.25 mg/ml in a drug formulation solutions that was used to prepare a dissolvable lyophilized formulation. On the contrary, introduction of some osmotic regulators, such as $CaCl_2$, reduced the concentration of hepalatide in the drug formulation that could be re-dissolved after lyophilization.

TABLE 6

Clarity of drug formulation re-dissolved after lyophilizing formulation solutions containing different osmotic regulators

| Hepalatide Concentration (mg/ml) | Osmotic Regulator | | | | |
|---|---|---|---|---|---|
| | Not contained | Glucose (5%) | NaCl (0.9%) | MgCl$_2$ (100 mM) | CaCl$_2$ (100 mM) |
| 0 | clear | clear | clear | clear | clear |
| 0.1 | <1 | <1 | <1 | <1 | >1 |
| 0.25 | >1 | <1 | <1 | <1 | >1 |
| 0.5 | >1 | >1 | >1 | >1 | >1 |
| 1.0 | >1 | >1 | >1 | >1 | >1 |
| 2.1 | >1 | >1 | >1 | >1 | >1 |
| 4.2 | >1 | >1 | >1 | >1 | >1 |
| 8.0 | >1 | >1 | >1 | >1 | >1 |
| 10.0 | >1 | >1 | >1 | >1 | >1 |

Note:
<1 indicates that turbidity is less than that of No. 1 standard solution while >1 indicates that turbidity is greater than that of No. 1 standard solution.

EXAMPLE 10: SCREEN OF EXCIPIENT FOR FORMULATION SOLUTION (I)

$Na_2HPO_4$—$NaH_2PO_4$ buffer (0.1M, pH=7.4) was prepared, which contained 2.1 mg/ml hepalatide, and 4% (W/V) mannitol, dextran, sorbitol, lactose, or polyethylene glycol (PEG 8000) as an excipient, respectively. Formulation solution without recipient was also prepared. The formulation solutions were placed in an incubator for incubation at 37° C. The stability of hepalatide of the solutions was detected at each time point according to the method described in Example 1. The formulation solutions were also lyophilized according to the method described in Example 7 and appearance of the lyophilized formulations was observed.

2. Experimental Result

Stability of hepalatide in phosphate buffer with or without excipient and appearance of the lyophilized formulations were shown in Table 7. Evaluated with the stability and the appearance of the lyophilized formulations, the formulation solution preferably does not contain an excipient, or mannitol, or dextran, more preferably contains mannitol or dextran as an excipient, or does not contain an excipient, or further more preferably contains mannitol as an excipient.

mental results, introduction of a solute, such as a recipient such as mannitol, dextran or sorbitol, etc., merely increased the concentration of hepalatide from 0-0.1 mg/ml to 0-0.25 mg/ml in a drug formulation solutions that was used to prepare a dissolvable lyophilized formulation, slightly increasing the concentration of hepalatide in a drug formulation that could be re-dissolved after lyophilization. Addition of some excipients, such as lactose, exhibited no great effect on the concentration of hepalatide in the drug formulation that could be re-dissolved after lyophilization, whereas addition of some recipients, such as polyethylene glycol, reduced the concentration of hepalatide in the drug formulation that could be re-dissolved after lyophilization.

TABLE 7

Purity (%) of hepalatide in formulation solutions of buffer with excipient and lyophilization appearance of the formulations

| Time Point (hour) | Excipient | | | | | |
|---|---|---|---|---|---|---|
| | Not contained | mannitol | dextran | sorbitol | lactose | polyethylene glycol |
| 0 | 99.4 | 99.4 | 99.4 | 99.4 | 99.4 | 99.4 |
| 4 | 99.4 | 99.4 | 99.4 | 98.3 | 98.7 | 98.1 |
| 8 | 99.2 | 99.3 | 99.2 | 97.5 | 97.9 | 94.9 |
| 12 | 99.0 | 99.1 | 99.1 | 97.0 | 97.1 | 92.6 |
| 16 | 98.7 | 98.8 | 98.5 | 96.5 | 97.1 | 91.2 |
| 24 | 98.5 | 98.7 | 98.6 | 95.7 | 96.8 | 85.5 |
| Appearance after lyophilization | Loose, massive | Compact, massive | Compact, massive | Relatively compact, massive | Relatively compact, massive | Relatively compact, massive |

EXAMPLE 11: SCREEN OF EXCIPIENT FOR FORMULATION SOLUTION (II)

1. Experimental Method

Other solutes, such as excipient, were added to investigate how to improve the re-dissolution of the lyophilized formulation to allow increased concentration of hepalatide for the formulation solution. $Na_2HPO_4$—$NaH_2PO_4$ buffer (0.1M, pH=7.4) was prepared, which contained hepalatide in an amount of 0, 0.1, 0.25, 0.5, 1.0, 2.1, 4.2, 8, or 10 mg/ml, and 4% (W/V) mannitol, dextran, sorbitol, lactose, or polyethylene glycol (PEG 8000) as an excipient, respectively. Formulation solution without recipient was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 8. As shown in the experi-

TABLE 8

Clarity of drug formulation re-dissolved after lyophilizing formulation solutions containing different recipients

| Hepalatide Concentration (mg/ml) | Excipient | | | | | |
|---|---|---|---|---|---|---|
| | Not contained | mannitol | dextran | sorbitol | lactose | polyethylene glycol |
| 0 | clear | clear | clear | clear | clear | clear |
| 0.1 | <1 | <1 | <1 | <1 | <1 | >1 |
| 0.25 | >1 | <1 | <1 | <1 | >1 | >1 |
| 0.5 | >1 | >1 | >1 | >1 | >1 | >1 |
| 1.0 | >1 | >1 | >1 | >1 | >1 | >1 |
| 2.1 | >1 | >1 | >1 | >1 | >1 | >1 |
| 4.2 | >1 | >1 | >1 | >1 | >1 | >1 |
| 8.0 | >1 | >1 | >1 | >1 | >1 | >1 |
| 10.0 | >1 | >1 | >1 | >1 | >1 | >1 |

Note:
<1 indicates that turbidity is less than that of No. 1 standard solution while >1 indicates that turbidity is greater than that of No. 1 standard solution.

EXAMPLE 12: EFFECT OF A COMBINATION OF EXCIPIENT AND OSMOTIC REGULATOR ON THE RE-DISSOLUTION PROPERTY OF A LYOPHILIZED FORMULATION

1. Experimental Method $Na_2HPO_4$—$NaH_2PO_4$ buffer (0.1M, pH=7.4) was prepared, which contained hepalatide in an amount of 0.1 mg/ml; and 4% (W/V) mannitol, dextran, sorbitol, lactose, or polyethylene glycol (PEG 8000) as an excipient, respectively; and glucose, NaCl, $MgCl_2$ or $CaCl_2$ as an osmotic regulator in a final concentration of 5% (W/V), 0.9% (W/V), 100 mM and 100 mM, respectively. Formulation solutions without osmotic regulator or excipient were also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 9. According to the experimental data, addition of PEG, or combinations of mannitol with NaCl, lactose with NaCl, or mannitol with $CaCl_2$, or $CaCl_2$ alone produced reduced clarity for the formulation solutions containing 0.1 mg/ml hepalatide after they were lyophilized and re-dissolved. On the contrary, a combination of sorbitol with other osmotic regulators, or a combination of glucose with other excipients could possibly improve the concentration of hepalatide in the drug formulation solution used to prepare a dissolvable lyophilized formulation.

TABLE 9

Clarity of drug formulation re-dissolved after lyophilizing formulation solutions containing different osmotic regulators and different recipients (hepalatide concentration of 0.1 mg/ml

| Hepalatide Concentration (mg/ml) | Osmotic Regulator Not contained | Glucose (5%) | NaCl (0.9%) | $MgCl_2$ (100 mM) | $CaCl_2$ (100 mM) |
|---|---|---|---|---|---|
| Not contained | <1 | <1 | <1 | <1 | >1 |
| mannitol | <1 | clear | >1 | <1 | >1 |
| dextran | <1 | clear | <1 | <1 | <1 |
| sorbitol | <1 | clear | clear | <1 | <1 |
| lactose | <1 | clear | >1 | <1 | <1 |
| polyethylene glycol | >1 | >1 | >1 | >1 | >1 |

Note:
<1 indicates that turbidity is less than that of No. 1 standard solution while >1 indicates that turbidity is greater than that of No. 1 standard solution.

EXAMPLE 13: SCREEN OF SORBITOL COMBINATION AND GLUCOSE COMBINATION

According to the pharmacodynamical calculation, the dose for a single human use is 4.2 mg. The drug will be administered by subcutaneous injection. Generally, the volume for subcutaneous injection is controlled within 2 ml. If the administration volume is greater than 2 ml, the drug will be administrated by multi-point injection. This is not convenient for clinical use and brings more suffering to the patients. Therefore, the target administration volume for the present formulation is 2 ml, that is to say, the target concentration of the drug in the formulation is 2.1 mg/ml. Sorbitol combination and glucose combination were screened based on this drug concentration.

1. Experimental Method $Na_2HPO_4$—$NaH_2PO_4$ buffer (0.1M, pH=7.4) was prepared, which contained hepalatide in an amount of 2.1 mg/ml. Two sets of combination solutions were prepared. For set 1, they contained 4% (W/V) sorbitol as recipient and glucose, NaCl, $MgCl_2$ or $CaCl_2$ as an osmotic regulator in a final concentration of 5% (W/V), 0.9% (W/V), 100 mM and 100 mM, respectively. For set 2, they contained 5% (W/V) glucose as an osmotic regulator, and 4% (W/V) mannitol, dextran, sorbitol, or lactose as an excipient. Formulation solutions without osmotic regulator or excipient were also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Tables 10 and 11. According to the data, the drug formulations containing 2.1 mg/ml hepalatide prepared from the sorbitol combinations or the glucose combinations could not be re-dissolved after lyophilization. Therefore, the sorbitol combinations or the glucose combinations are unable to increase the concentration of hepalatide to 2.1 mg/ml in a drug formulation solution used to prepare a dissolvable lyophilized formulation. Study on screen of hepalatide formulation came to a deadlock.

TABLE 10

Clarity of drug formulation re-dissolved after lyophilizing formulation solutions containing glucose and different recipients

| | Excipient Not contained | mannitol | dextran | sorbitol | lactose |
|---|---|---|---|---|---|
| Glucose combination | >1 | >1 | >1 | >1 | >1 |

Note:
<1 indicates that turbidity is less than that of No. 1 standard solution while >1 indicates that turbidity is greater than that of No. 1 standard solution.

TABLE 11

Clarity of drug formulation re-dissolved after lyophilizing formulation solutions containing sorbitol and different osmotic regulators

| | Osmotic Regulator Not contained | Glucose (5%) | NaCl (0.9%) | $MgCl_2$ (100 mM) | $CaCl_2$ (100 mM) |
|---|---|---|---|---|---|
| Sorbitol combination | >1 | >1 | >1 | >1 | >1 |

Note:
<1 indicates that turbidity is less than that of No. 1 standard solution while >1 indicates that turbidity is greater than that of No. 1 standard solution.

EXAMPLE 14: SURPRISING DISCOVERY ON METHOD FOR INCREASING THE CONCENTRATION OF HEPALATIDE IN A DRUG FORMULATION THAT COULD BE RE-DISSOLVED AFTER LYOPHILIZATION

Solubility of hepalatide in physiological saline, i.e., NaCl solution (0.9%, W/V), was detected in Example 1, showing that hepalatide was hardly soluble in physiological saline. Introduction of NaCl for improving the re-dissolution of a lyophilized formulation was investigated in Example 9. Results showed that addition of NaCl merely increased the concentration of hepalatide from 0-0.1 mg/ml to 0-0.25 mg/ml in a drug formulation solution used to prepare a dissolvable lyophilized formulation. The results in Example 12 showed that the lyophilized formulation could not be commendably dissolved by using a combination of mannitol and NaCl, even if hepalatide was present merely in an amount of 0.1 mg/ml. However, it was surprisingly found that the lyophilized formulation prepared from a formulation solution containing mannitol and NaCl and high concentration of hepalatide exhibited an excellent re-dissolution property. Specific experiments were showed below.

1. Experimental Method $Na_2HPO_4$—$NaH_2PO_4$ buffer (0.1M, pH=7.4) was prepared, which contained hepalatide in an amount of 0, 0.1, 0.25, 0.5, 1.0, 2.1, 4.2, 8, or 10 mg/ml; NaCl in a final concentration of 0.9% (W/V); and mannitol in a final concentration of 4% (W/V). Formulation solution without mannitol and NaCl was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 12. The concentration of hepalatide for the formulation containing both mannitol and NaCl that could be re-dissolved (to be a clear solution, or with turbidity less than that of No. 1 standard solution) after lyophilization was in the range of from 0.25 mg/ml to 8 mg/ml, which fully satisfied the requirements on clinical use and the related requirements in the Chinese Pharmacopoeia. In an obvious contrast to it, introduction of only one solute molecule, NaCl or mannitol, merely increased the concentration of hepalatide from 0-0.1 mg/ml to 0-0.25 mg/ml in a drug formulation solution used to prepare a dissolvable lyophilized formulation. And, the formulation solution containing a low hepalatide concentration (0.1 mg/ml) could not be re-dissolved after preparation into a lyophilized formulation. From this Example, the hepalatide concentration in the formulation solution is preferably from 0.1 mg/ml to 8.0 mg/ml, more preferably from 0.5 mg/ml to 5.0 mg/ml, more preferably from 1.0 mg/ml to 2.1 mg/ml, more preferably from 2.0 mg/ml to 2.1 mg/ml. Preferably, the hepalatide concentration is 0.25 mg/ml, or 0.5 mg/ml, or 1.0 mg/ml, or 2.0 mg/ml, or 2.1 mg/ml, or 4.0 mg/ml, or 4.2 mg/ml, or 5.0 mg/ml, or 10.0 mg/ml, more preferably 2.0 mg/ml or 2.1 mg/ml, and further more preferably 2.1 mg/ml.

It is generally believed that the drug molecule is not prone to form polymers under low concentration and thus is readily to be dissolved after lyophilization. Results in Examples 7, 9 and 11 of the present disclosure also support this general knowledge. However, the specific knowledge about hepalatide obtained in this Example (i.e., in the presence of both mannitol and NaCl, the drug formulation containing a low concentration of hepalatide is difficult to be dissolved after lyophilization, whereas the drug formulation containing a high concentration of hepalatide is readily to be dissolved after lyophilization) is contrary to the general knowledge, indicating that hepalatide molecule exhibits a different special attribute from the other drug molecules. It is unknown why hepalatide exhibits such a special attribute and this attribute is difficult to be predicted. As a result, it is also difficult to predict which formulation component(s) could increase the concentration of hepalatide in a drug formulation solution used to prepare a dissolvable lyophilized formulation.

TABLE 12

Clarity of drug formulation re-dissolved after lyophilizing the formulation solution containing mannitol and NaCl

| NaCl/mannitol Content | Hepalatide Concentration(mg/ml) | | | | | | | | |
|---|---|---|---|---|---|---|---|---|---|
| | 0 | 0.1 | 0.25 | 0.5 | 1.0 | 2.1 | 4.2 | 8 | 10 |
| NaCl (0%); Mannitol (0%) | clear | <1 | >1 | >1 | >1 | >1 | >1 | >1 | >1 |
| NaCl (0.9%); Mannitol (4%) | clear | >1 | clear | clear | clear | clear | clear | <1 | >1 |
| NaCl (0.9%); Mannitol (0%)* | clear | <1 | <1 | >1 | >1 | >1 | >1 | >1 | >1 |
| NaCl (0%); Mannitol (4%)# | clear | <1 | <1 | >1 | >1 | >1 | >1 | >1 | >1 |

Note:
*results obtained in Example 9;
- results obtained in Example 11;
<1 indicates that turbidity is less than that of No. 1 standard solution while >1 indicates that turbidity is greater than that of No. 1 standard solution.

EXAMPLE 15: SCREEN OF COMBINATION OF EXCIPIENT AND OSMOTIC REGULATOR (I)

According to the knowledge obtained in Example 14, other combinations of excipient and osmotic regulator were tested to find if there were better combinations to increase the concentration of hepalatide in the drug formulation solution used to prepare a dissolvable lyophilized formulation.

1. Experimental Method $Na_2HPO_4$—$NaH_2PO_4$ buffer (0.1M, pH=7.4) was prepared, which contained hepalatide in an amount of 0, 0.1, 0.25, 0.5, 1.0, 2.1, 4.2, 8, or 10 mg/ml; NaCl in a final concentration of 0.9% (W/V); and 4% (W/V) mannitol, dextran, sorbitol, lactose, or polyethylene glycol (PEG 8000) as an excipient. Formulation solution without excipient was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 13. It was found that combination of NaCl and dextran and combination of NaCl and sorbitol could increase the hepalatide concentration to some extent in the drug formulation solution used to prepare a dissolvable lyophilized formulation.

TABLE 13

Clarity of drug formulation re-dissolved after lyophilizing the formulation solution containing NaCl and different excipients

| Hepalatide Concentration (mg/ml) | Excipient | | | | | |
|---|---|---|---|---|---|---|
| | Not contained | mannitol | dextran | sorbitol | lactose | polyethylene glycol |
| 0 | clear | clear | clear | clear | clear | clear |
| 0.1 | <1 | >1 | <1 | clear | >1 | >1 |
| 0.25 | <1 | clear | <1 | clear | >1 | >1 |
| 0.5 | >1 | clear | <1 | <1 | >1 | >1 |
| 1.0 | >1 | clear | <1 | >1 | >1 | >1 |
| 2.1 | >1 | clear | >1 | >1 | >1 | >1 |
| 4.2 | >1 | clear | >1 | >1 | >1 | >1 |
| 8.0 | >1 | <1 | >1 | >1 | >1 | >1 |
| 10.0 | >1 | >1 | >1 | >1 | >1 | >1 |

Note:
<1 indicates that turbidity is less than that of No. 1 standard solution while >1 indicates that turbidity is greater than that of No. 1 standard solution.

EXAMPLE 16: SCREEN OF COMBINATION OF EXCIPIENT AND OSMOTIC REGULATOR (II)

1. Experimental Method $Na_2HPO_4$—$NaH_2PO_4$ buffer (0.1M, pH=7.4) was prepared, which contained hepalatide in an amount of 0, 0.1, 0.25, 0.5, 1.0, 2.1, 4.2, 8, or 10 mg/ml; mannitol in a final concentration of 4% (W/V); and glucose, NaCl, $MgCl_2$ or $CaCl_2$ as an osmotic regulator in a final concentration of 5% (W/V), 0.9% (W/V), 100 mM and 100 mM, respectively. Formulation solution without osmotic regulator was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 14. It was found that the combination of mannitol and glucose could increase the hepalatide concentration to some extent in the drug formulation solution used to prepare a dissolvable lyophilized formulation.

TABLE 14

Clarity of drug formulation re-dissolved after lyophilizing the formulation solution containing mannitol and different osmotic regulators

| Hepalatide Concentration (mg/ml) | Osmotic Regulator | | | | |
|---|---|---|---|---|---|
| | Not contained | Glucose (5%) | NaCl (0.9%) | $MgCl_2$ (100 mM) | $CaCl_2$ (100 mM) |
| 0 | clear | clear | clear | clear | clear |
| 0.1 | <1 | clear | >1 | <1 | >1 |
| 0.25 | <1 | clear | clear | <1 | >1 |
| 0.5 | >1 | <1 | clear | >1 | >1 |
| 1.0 | >1 | <1 | clear | >1 | >1 |
| 2.1 | >1 | >1 | clear | >1 | >1 |
| 4.2 | >1 | >1 | clear | >1 | >1 |
| 8.0 | >1 | >1 | <1 | >1 | >1 |
| 10.0 | >1 | >1 | >1 | >1 | >1 |

Note:
<1 indicates that turbidity is less than that of No. 1 standard solution while >1 indicates that turbidity is greater than that of No. 1 standard solution.

EXAMPLE 17: SCREEN OF COMBINATION OF EXCIPIENT AND OSMOTIC REGULATOR (III)

1. Experimental Method $Na_2HPO_4$—$NaH_2PO_4$ buffer (0.1M, pH=7.4) was prepared, which contained hepalatide in an amount of 0.25, 1.0, or 2.1 mg/ml; 4% (W/V) mannitol, dextran, sorbitol, lactose, or polyethylene glycol (PEG 8000) as recipient; and glucose, NaCl, $MgCl_2$ or $CaCl_2$ as an osmotic regulator in a final concentration of 5% (W/V), 0.9% (W/V), 100 mM and 100 mM, respectively. Formulation solution without osmotic regulator or excipient was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Tables 15-17. The data in Table 15 showed that many combinations of excipient and osmotic regulator could increase the hepalatide concentration to 0.25 mg/ml in the drug formulation solution used to prepare a dissolvable lyophilized formulation. The data in Table 16 showed that the combinations of the excipient mannitol, dextran, sorbitol and the osmotic regulator glucose, NaCl could increase the hepalatide concentration to 1 mg/ml in the drug formulation solution used to prepare a dissolvable lyophilized formulation. The data in Table 17 showed that the combination of the excipient mannitol and the osmotic regulator NaCl could increase the hepalatide concentration to 2.1 mg/ml in the drug formulation solution used to prepare a dissolvable lyophilized formulation.

TABLE 15

Clarity of drug formulation re-dissolved after lyophilizing the formulation solution containing different osmotic regulators and excipients (hepalatide concentration of 0.25 mg/ml)

| Hepalatide Concentration (mg/ml) | Osmotic Regulator | | | | |
|---|---|---|---|---|---|
| | Not contained | Glucose (5%) | NaCl (0.9%) | $MgCl_2$ (100 mM) | $CaCl_2$ (100 mM) |
| Not contained | >1 | <1 | <1 | <1 | >1 |
| mannitol | <1 | clear | clear | <1 | >1 |
| dextran | <1 | clear | <1 | >1 | <1 |
| sorbitol | <1 | clear | clear | <1 | >1 |

TABLE 15-continued

Clarity of drug formulation re-dissolved after lyophilizing the formulation solution containing different osmotic regulators and excipients (hepalatide concentration of 0.25 mg/ml)

| Hepalatide | Osmotic Regulator | | | | |
|---|---|---|---|---|---|
| Concentration (mg/ml) | Not contained | Glucose (5%) | NaCl (0.9%) | MgCl$_2$ (100 mM) | CaCl$_2$ (100 mM) |
| lactose | >1 | >1 | >1 | >1 | <1 |
| polyethylene glycol | >1 | >1 | >1 | >1 | >1 |

Note:
<1 indicates that turbidity is less than that of No. 1 standard solution while >1 indicates that turbidity is greater than that of No. 1 standard solution.

TABLE 16

Clarity of drug formulation re-dissolved after lyophilizing the formulation solution containing different osmotic regulators and excipients (hepalatide concentration of 1 mg/ml)

| Hepalatide | Osmotic Regulator | | | | |
|---|---|---|---|---|---|
| Concentration (mg/ml) | Not contained | Glucose (5%) | NaCl (0.9%) | MgCl$_2$ (100 mM) | CaCl$_2$ (100 mM) |
| Not contained | >1 | >1 | >1 | >1 | >1 |
| mannitol | >1 | <1 | clear | >1 | >1 |
| dextran | >1 | <1 | <1 | >1 | >1 |
| sorbitol | >1 | <1 | >1 | >1 | >1 |
| lactose | >1 | >1 | >1 | >1 | >1 |
| polyethylene glycol | >1 | >1 | >1 | >1 | >1 |

Note:
<1 indicates that turbidity is less than that of No. 1 standard solution while >1 indicates that turbidity is greater than that of No. 1 standard solution.

TABLE 17

Clarity of drug formulation re-dissolved after lyophilizing the formulation solution containing different osmotic regulators and excipients (hepalatide concentration of 2.1 mg/ml)

| Hepalatide | Osmotic Regulator | | | | |
|---|---|---|---|---|---|
| Concentration (mg/ml) | Not contained | Glucose (5%) | NaCl (0.9%) | MgCl$_2$ (100 mM) | CaCl$_2$ (100 mM) |
| Not contained | >1 | >1 | >1 | >1 | >1 |
| mannitol | >1 | >1 | clear | >1 | >1 |
| dextran | >1 | >1 | >1 | >1 | >1 |
| sorbitol | >1 | >1 | >1 | >1 | >1 |
| lactose | >1 | >1 | >1 | >1 | >1 |
| polyethylene glycol | >1 | >1 | >1 | >1 | >1 |

Note:
<1 indicates that turbidity is less than that of No. 1 standard solution while >1 indicates that turbidity is greater than that of No. 1 standard solution.

EXAMPLE 18: SCREEN OF COMBINATION OF EXCIPIENT AND OSMOTIC REGULATOR (IV)

1. Experimental Method

Na$_2$CO$_3$—NaHCO$_3$ buffer (0.1M, pH=10.0) was prepared, which contained hepalatide in an amount of 2.1 mg/ml; 4% (W/V) mannitol, dextran, sorbitol, lactose, or polyethylene glycol (PEG 8000) as recipient; and glucose, NaCl, MgCl$_2$ or CaCl$_2$ as an osmotic regulator in a final concentration of 5% (W/V), 0.9% (W/V), 100 mM and 100 mM, respectively. Formulation solution without osmotic regulator or excipient was also prepared. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The above drug formulation solutions were loaded into glass bottles in an amount of 1 ml/bottle and re-dissolved with injectable water to 1 ml/bottle after lyophilization. The detection result on clarity of the re-constructed formulation solutions was shown in Table 18. The data showed that in the carbonate buffer, the combination of the excipient mannitol and the osmotic regulator NaCl could increase the hepalatide concentration to 2.1 mg/ml in the drug formulation solution used to prepare a dissolvable lyophilized formulation.

TABLE 18

Clarity of drug formulation re-dissolved after lyophilizing the formulation solution containing different osmotic regulators and excipients (hepalatide concentration of 2.1 mg/ml)

| Hepalatide | Osmotic Regulator | | | | |
|---|---|---|---|---|---|
| Concentration (mg/ml) | Not contained | Glucose (5%) | NaCl (0.9%) | MgCl$_2$ (100 mM) | CaCl$_2$ (100 mM) |
| Not contained | >1 | >1 | >1 | >1 | >1 |
| mannitol | >1 | >1 | clear | >1 | >1 |
| dextran | >1 | >1 | >1 | >1 | >1 |
| sorbitol | >1 | >1 | >1 | >1 | >1 |
| lactose | >1 | >1 | >1 | >1 | >1 |
| polyethylene glycol | >1 | >1 | >1 | >1 | >1 |

Note:
<1 indicates that turbidity is less than that of No. 1 standard solution while >1 indicates that turbidity is greater than that of No. 1 standard solution.

EXAMPLE 19: SCREEN OF PHOSPHATE BUFFER SALT SOLUTION

1. Experimental Method

Solutions of phosphate buffer salt were prepared, in which the molar concentration of phosphate was from 0.001M to 0.5M, and the molar ratio between Na$_2$HPO$_4$ and NaH$_2$PO$_4$ was from 0:100 to 100:0. The buffers also contained 116 mM of NaCl, 4% (W/V) of mannitol and 2.1 mg/ml of hepalatide and were formulated with water. Detection of pH value was conducted according to the requirements on pH detection described in appendix VI H of Chinese Pharmacopoeia, 2010, Volume II by using PB-10 type pH meter (Sartorius, USA). Stability of hepalatide in the formulation solution was detected according to the method for detecting purity as described in Example 1.

2. Experimental Result

The pH values of each formulation solution were shown in Table 19. The pH physiological range of a human being is from 7.34 to 7.45. Formulation solutions having a pH close to the physiological range are preferred (see the dark portion). The initial purity of hepalatide in each formulation solution was 99.4%. Purity detected by HPLC 24 hours after incubation at 37° C. was shown in Table 20. Formulation solutions having an excellent stability are preferred (see the dart portion). By considering both the pH value and stability of the formulation solution, in the preferred formulation solutions the molar concentration of the phosphate is from 0.001M to 0.1M, more preferably from 0.02M to 0.05M, more preferably 0.02M. The molar ratio between Na$_2$HPO$_4$ and NaH$_2$PO$_4$ is preferably from 70:30 to 95:5, more preferable from 81:19 to 95:5, and further more preferably 90:10.

TABLE 19 pH values of hepalatide in phosphate buffer

| Concentration of phosphate radical (M) | Ratio between Na$_2$HPO$_4$ and NaH$_2$PO$_4$ | | | | | | | |
|---|---|---|---|---|---|---|---|---|
|  | 0:100 | 30:70 | 50:50 | 70:30 | 81:19 | 90:10 | 95:5 | 100:0 |
| 0.001 | 5.02 | 5.35 | 5.57 | 5.96 | 6.23 | 6.51 | 6.60 | 6.82 |
| 0.01 | 5.45 | 5.60 | 5.68 | 6.23 | 7.01 | 7.07 | 7.09 | 7.11 |
| 0.02 | 5.52 | 6.07 | 6.07 | 6.60 | 7.10 | 7.36 | 7.49 | 7.62 |
| 0.05 | 5.59 | 6.16 | 6.32 | 6.72 | 7.18 | 7.47 | 7.70 | 7.89 |
| 0.10 | 5.62 | 6.28 | 6.57 | 7.02 | 7.15 | 7.52 | 7.74 | 7.90 |
| 0.20 | 5.65 | 6.35 | 6.63 | 7.14 | 7.29 | 7.60 | 7.81 | 7.92 |
| 0.50 | 5.68 | 6.39 | 6.81 | 7.20 | 7.39 | 7.65 | 7.88 | 8.01 |

TABLE 20

Purity (%) of hepalatide in phosphate buffer 24 hours after incubation at 37□

| Concentration of phosphate radical (M) | Ratio between Na$_2$HPO$_4$ and NaH$_2$PO$_4$ | | | | | | | |
|---|---|---|---|---|---|---|---|---|
| (M) | 0:100 | 30:70 | 50:50 | 70:30 | 81:19 | 90:10 | 95:5 | 100:0 |
| 0.001 | 98.3 | 98.7 | 98.6 | 99.1 | 99.2 | 99.3 | 99.3 | 99.2 |
| 0.01 | 98.5 | 98.7 | 98.9 | 99.2 | 99.4 | 99.3 | 99.3 | 99.4 |
| 0.02 | 99.0 | 99.0 | 99.2 | 99.3 | 99.4 | 99.4 | 99.3 | 99.2 |
| 0.05 | 98.7 | 98.8 | 99.0 | 99.3 | 99.4 | 99.4 | 99.3 | 99.2 |
| 0.10 | 98.2 | 98.4 | 98.5 | 98.6 | 98.7 | 99.3 | 99.1 | 98.6 |
| 0.20 | 97.4 | 97.5 | 97.6 | 98.1 | 98.5 | 98.5 | 98.2 | 97.9 |
| 0.50 | 96.8 | 97.0 | 97.2 | 97.7 | 97.9 | 97.7 | 97.5 | 97.3 |

EXAMPLE 20: SCREEN OF CONCENTRATION OF OSMOTIC REGULATOR NaCl IN FORMULATION SOLUTION

1. Experimental Method

Formulation solutions were formulated with water, containing 0.02M phosphate buffer salt with a molar ratio between Na$_2$HPO$_4$:NaH$_2$PO$_4$ of 90:10, 4% (W/V) mannitol, and NaCl in a molar concentration from 0 mM to 500 mM. Hepalatide was added into each solution to obtain a final concentration of 2.1 mg/ml. Detection of pH value was conducted according to the requirements on pH detection described in appendix VI H of Chinese Pharmacopoeia, 2010, Volume II by using PB-10 type pH meter (Sartorius, USA). Solubility of hepalatide in the formulation solutions was detected according to the method for detecting solubility as described in Example 2. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The pH values and solubility of formulation solutions containing different concentrations of NaCl were shown in Table 21. Evaluated with the pH value, solubility and re-dissolution after lyophilization, the NaCl concentration in the formulation solution is preferably from 50 mM to 200 mM, more preferably from 116 mM to 154 mM, further more preferably 116 mM.

TABLE 21 pH and solubility of hepalatide in different NaCl concentration and clarity re-dissolved solution after lyophilization

| NaCl Concentration (mM) | pH Value | Solubility | Clarity |
|---|---|---|---|
| 0 | 7.63 | Completely dissolved | >1 |
| 50 | 7.51 | Completely dissolved | <1 |
| 116 | 7.38 | Completely dissolved | clear |
| 154 | 7.28 | Completely dissolved | clear |
| 200 | 7.17 | Completely dissolved | clear |
| 300 | 6.81 | Completely dissolved | clear |
| 500 | 6.69 | Partially dissolved | >1 |

Note:
<1 indicates that turbidity is less than that of No. 1 standard solution while >1 indicates that turbidity is greater than that of No. 1 standard solution.

EXAMPLE 21: SCREEN OF HEPALATIDE CONCENTRATION IN FORMULATION SOLUTIONS

1. Experimental Method

Formulation solution was formulated with water, containing 0.02M phosphate buffer salt with a molar ratio between Na$_2$HPO$_4$:NaH$_2$PO$_4$ of 90:10, 4% (W/V) mannitol, and 116 mM NaCl. Hepalatide was added into the solution to obtain a final concentration of from 0.1 to 10 mg/ml. Detection was conducted according to the requirements on pH detection described in appendix VI H of Chinese Pharmacopoeia, 2010, Volume II by using PB-10 type pH meter (Sartorius, USA). Solubility of hepalatide in the formulation solutions was detected according to the method for detecting solubility as described in Example 2. Since formation of foam during stirring to dissolve the polypeptide may influence the subsequent process of preparation, formation of foam was observed during formulating the formulation solutions. The above formulation solutions were loaded into glass bottles in an amount of 1 ml/bottle and lyophilized according to the lyophilization procedure described in Example 7. The re-dissolution of the lyophilized drug formulation after re-dissolving was observed according to the method for detecting clarity described in Example 7.

2. Experimental Result

The pH, solubility, formation of foam and re-dissolution after lyophilization of formulation solutions containing different concentrations of hepalatide were shown in Table 22. Evaluated with these four aspects, the concentration of hepalatide in the formulation solution is preferably from 0.25 mg/ml to 8.0 mg/ml, more preferably from 0.25 mg/ml to 5.0 mg/ml, more preferably from 1.0 mg/ml to 2.1 mg/ml, further more preferably from 2.0 mg/ml to 2.1 mg/ml. Preferably, the fixed concentration of hepalatide in formulation solution is 0.25 mg/ml, or 0.5 mg/ml, or 1.0 mg/ml, or 2.0 mg/ml, or 2.1 mg/ml, or 4.0 mg/ml, or 4.2 mg/ml, or 5.0 mg/ml, or 8.0 mg/ml, more preferably 2.0 mg/ml or 2.1 mg/ml, and further more preferably 2.1 mg/ml.

TABLE 22 pH, solubility and formation of foam of formulation solutions containing different concentrations of hepalatide

| Hepalatide Concentration (mg/ml) | pH Value | Solubility | Formulation of Foam | Clarity |
|---|---|---|---|---|
| 0 | 7.40 | — | None | clear |
| 0.1 | 7.41 | Completely dissolved | None | >1 |
| 0.25 | 7.41 | Completely dissolved | None | clear |
| 0.5 | 7.39 | Completely dissolved | Slight | clear |
| 1.0 | 7.37 | Completely dissolved | Slight | clear |
| 2.0 | 7.34 | Completely dissolved | A small amount | clear |
| 2.1 | 7.30 | Completely dissolved | A small amount | clear |
| 4.0 | 7.25 | Completely dissolved | A major amount | clear |
| 4.2 | 7.23 | Completely dissolved | A major amount | clear |
| 5.0 | 7.18 | Completely dissolved | A major amount | clear |
| 8.0 | 7.04 | Completely dissolved | A major amount | <1 |
| 10.0 | 7.03 | Completely dissolved | A great amount | >1 |

Note:
<1 indicates that turbidity is less than that of No. 1 standard solution while >1 indicates that turbidity is greater than that of No. 1 standard solution.

EXAMPLE 22: SCREEN OF MANNITOL CONCENTRATION IN FORMULATION SOLUTION

1. Experimental Method

Formulation solutions were formulated with water, containing 0.02M phosphate buffer salt with a molar ratio between $Na_2HPO_4:NaH_2PO_4$ of 90:10, mannitol in a concentration of from 0% (W/V) to 25% (W/V), 116 mM NaCl, and 2.1 mg/ml hepalatide. Detection was conducted according to the requirements on pH detection described in appendix VI H of Chinese Pharmacopoeia, 2010, Volume II by using PB-10 type pH meter (Sartorius, USA). Solubility of hepalatide in the formulation solutions was detected according to the method for detecting solubility as described in Example 2. The formulation solutions were loaded into a 2 ml glass bottles for lyophilization with 1 ml/bottle. The bottles were then placed into the cabinet of cryogenic freezing dryer (Supermodulyo, 0.4 m2, E-C Apparatus) for lyophilization according to the procedure described in Example 7 and then plugged and capped. The lyophilized formulations were re-dissolved with 1 ml injectable water and detected for the re-dissolution of the lyophilized drug formulation according to the method for detecting clarity described in Example 7. The lyophilized formulations were incubated in an incubator at 37° C. 8 weeks later formulations in each bottle were re-dissolved with 1 ml injectable water and then purity of hepalatide in each formulation solution was detected according to the method for detecting purity as described in Example 1.

2. Experimental Result

The pH values, appearance of lyophilized formulation and re-dissolution after lyophilization, and purity of hepalatide obtained after placing the lyophilized formulation at 37□ for 8 weeks, of the formulation solutions containing different concentrations of mannitol, were shown in Table 23. Purity of hepalatide detected after lyophilization of each formulation solution was 99.4%. By fully considering the pH of formulation solution, appearance of lyophilized formulation and stability of lyophilized formulation, the preferred concentration of mannitol in formulation solution is 0.5% to 15%, preferably from 1% to 5%, more preferably 4%. The lyophilized drug formulation could be re-dissolved with 1 ml to 5 ml injection water to reconstruct a liquid drug formulation.

TABLE 23 pH, appearance after lyophilization, time for re-dissolution and stability at week 8 of formulation solutions containing different mannitol concentrations

| Mannitol Concentration (%) | pH Value | Appearance after lyophilization | Time for re-dissolution (second) | Clarity | Hepalatide purity (week 8, %) |
|---|---|---|---|---|---|
| 0 | 7.44 | Loose, massive | 1 | >1 | 97.6 |
| 0.5 | 7.41 | Loose, massive | 1 | <1 | 98.7 |
| 1 | 7.39 | Relatively compact, massive | 1 | <1 | 98.9 |
| 2 | 7.37 | Relatively compact, massive | 2 | clear | 99.3 |
| 3 | 7.35 | Compact, massive | 3 | clear | 99.4 |
| 4 | 7.34 | Compact, massive | 3 | clear | 99.4 |
| 5 | 7.24 | Compact, massive | 3 | clear | 99.4 |
| 10 | 7.13 | Relatively solid, massive | 7 | <1 | 99.4 |
| 15 | 7.06 | Solid, caking | 30 | <1 | 99.3 |
| 20 | 6.84 | Solid, caking | 120 | >1 | 99.1 |

Note:
<1 indicates that turbidity is less than that of No. 1 standard solution while >1 indicates that turbidity is greater than that of No. 1 standard solution.

EXAMPLE 23: STERILIZATION OF FORMULATION SOLUTION BY FILTRATION

1. Experimental Method

The pH values, appearance of lyophilized formulation and re-dissolution after lyophilization, and purity of hepalatide obtained after placing the lyophilized formulation at 37° C. for 8 weeks, of the formulation solutions containing different concentrations of mannitol, were shown in Table 23. Purity of hepalatide detected after lyophilization of each formulation solution was 99.4%. By fully considering the pH of formulation solution, appearance of lyophilized formulation and stability of lyophilized formulation, the preferred concentration of mannitol in formulation solution is 0.5% to 15%, preferably from 1% to 5%, more preferably 4%. The lyophilized drug formulation could be re-dissolved with 1 ml to 5 ml injection water to reconstruct a liquid drug formulation.

2. Experimental Result

Formulation solutions of Examples 6 to 22 could all be filtered through 0.45 μm and 0.22 μm filter membranes for sterilization. After detection, no bacterial growth was detected. All formulation solutions were prepared into sterile drug formulations.

EXAMPLE 24: PREPARATION OF DRUG FORMULATION CONTAINING CORRESPONDING AMOUNT OF HEPALATIDE IN EACH BOTTLE

1. Experimental Method

1) Liquid drug formulations listed in any of the following component table were formulated with water, in which the molecular weights of $Na_2HPO_4 \cdot 12H_2O$, $NaH_2PO_4 \cdot 2H_2O$ and NaCl were calculated as 358.14, 156.01 and 58.4, respectively.

(a)

| Component | Concentration |
| --- | --- |
| Hepalatide | 8.0 mg/ml |
| mannitol | 4% (w/v) |
| $Na_2HPO_4$ | 18 mM |
| $NaH_2PO_4$ | 2 mM |
| NaCl | 116 mM |

When calculated in 1000 ml liquid formulation, the 1000 ml liquid formulation contains:

| Component | Weight |
| --- | --- |
| Hepalatide | 8.0 g |
| mannitol | 40 g |
| $Na_2HPO_4 \cdot 12H_2O$ | 6.4465 g |
| $NaH_2PO_4 \cdot 2H_2O$ | 0.3120 g |
| NaCl | 6.7744 g |

(b)

| Component | Concentration |
| --- | --- |
| Hepalatide | 5.0 mg/ml |
| mannitol | 4% (w/v) |
| $Na_2HPO_4$ | 18 mM |
| $NaH_2PO_4$ | 2 mM |
| NaCl | 116 mM |

When calculated in 1000 ml liquid formulation, the 1000 ml liquid formulation contains:

| Component | Weight |
| --- | --- |
| Hepalatide | 5.0 g |
| mannitol | 40 g |
| $Na_2HPO_4 \cdot 12H_2O$ | 6.4465 g |
| $NaH_2PO_4 \cdot 2H_2O$ | 0.3120 g |
| NaCl | 6.7744 g |

(c)

| Component | Concentration |
| --- | --- |
| Hepalatide | 4.1 mg/ml |
| mannitol | 4% (w/v) |
| $Na_2HPO_4$ | 18 mM |
| $NaH_2PO_4$ | 2 mM |
| NaCl | 116 mM |

When calculated in 1000 ml liquid formulation, the 1000 ml liquid formulation contains:

| Component | Weight |
| --- | --- |
| Hepalatide | 4.1 g |
| mannitol | 40 g |
| $Na_2HPO_4 \cdot 12H_2O$ | 6.4465 g |
| $NaH_2PO_4 \cdot 2H_2O$ | 0.3120 g |
| NaCl | 6.7744 g |

(d)

| Component | Concentration |
| --- | --- |
| Hepalatide | 4.0 mg/ml |
| mannitol | 4%(w/v) |
| $Na_2HPO_4$ | 18 mM |
| $NaH_2PO_4$ | 2 mM |
| NaCl | 116 mM |

When calculated in 1000 ml liquid formulation, the 1000 ml liquid formulation contains:

| Component | Weight |
| --- | --- |
| Hepalatide | 4.0 g |
| mannitol | 40 g |
| $Na_2HPO_4 \cdot 12H_2O$ | 6.4465 g |
| $NaH_2PO_4 \cdot 2H_2O$ | 0.3120 g |
| NaCl | 6.7744 g |

(e)

| Component | Concentration |
| --- | --- |
| Hepalatide | 2.1 mg/ml |
| mannitol | 4%(w/v) |
| $Na_2HPO_4$ | 18 mM |
| $NaH_2PO_4$ | 2 mM |
| NaCl | 116 mM |

When calculated in 1000 ml liquid formulation, the 1000 ml liquid formulation contains:

| Component | Weight |
| --- | --- |
| Hepalatide | 2.1 g |
| mannitol | 40 g |
| $Na_2HPO_4 \cdot 12H_2O$ | 6.4465 g |
| $NaH_2PO_4 \cdot 2H_2O$ | 0.3120 g |
| NaCl | 6.7744 g |

(f)

| Component | Concentration |
| --- | --- |
| Hepalatide | 2.0 mg/ml |
| mannitol | 4%(w/v) |
| Na$_2$HPO$_4$ | 18 mM |
| NaH$_2$PO$_4$ | 2 mM |
| NaCl | 116 mM |

When calculated in 1000 ml liquid formulation, the 1000 ml liquid formulation contains:

| Component | Weight |
| --- | --- |
| Hepalatide | 2.0 g |
| mannitol | 40 g |
| Na$_2$HPO$_4$·12H$_2$O | 6.4465 g |
| NaH$_2$PO$_4$·2H$_2$O | 0.3120 g |
| NaCl | 6.7744 g |

(g)

| Component | Concentration |
| --- | --- |
| Hepalatide | 1.0 mg/ml |
| mannitol | 4%(w/v) |
| Na$_2$HPO$_4$ | 18 mM |
| NaH$_2$PO$_4$ | 2 mM |
| NaCl | 116 mM |

When calculated in 1000 ml liquid formulation, the 1000 ml liquid formulation contains:

| Component | Weight |
| --- | --- |
| Hepalatide | 1.0 g |
| mannitol | 40 g |
| Na$_2$HPO$_4$·12H$_2$O | 6.4465 g |
| NaH$_2$PO$_4$·2H$_2$O | 0.3120 g |
| NaCl | 6.7744 g |

(h)

| Component | Concentration |
| --- | --- |
| Hepalatide | 0.5 mg/ml |
| mannitol | 4%(w/v) |
| Na$_2$HPO$_4$ | 18 mM |
| NaH$_2$PO$_4$ | 2 mM |
| NaCl | 116 mM |

When calculated in 1000 ml liquid formulation, the 1000 ml liquid formulation contains:

| Component | Weight |
| --- | --- |
| Hepalatide | 0.5 g |
| mannitol | 40 g |
| Na$_2$HPO$_4$·12H$_2$O | 6.4465 g |
| NaH$_2$PO$_4$·2H$_2$O | 0.3120 g |
| NaCl | 6.7744 g |

(i)

| Component | Concentration |
| --- | --- |
| Hepalatide | 0.25 mg/ml |
| mannitol | 4%(w/v) |
| Na$_2$HPO$_4$ | 18 mM |
| NaH$_2$PO$_4$ | 2 mM |
| NaCl | 116 mM |

When calculated in 1000 ml liquid formulation, the 1000 ml liquid formulation contains:

| Component | Weight |
| --- | --- |
| Hepalatide | 0.25 g |
| mannitol | 40 g |
| Na$_2$HPO$_4$·12H$_2$O | 6.4465 g |
| NaH$_2$PO$_4$·2H$_2$O | 0.3120 g |
| NaCl | 6.7744 g |

2) The above liquid drug formulations were filtered through 0.22 μm filter membrane for sterilization to obtain sterile formulations. Sterile detection was carried out according to the methods for sterile experiments described in Chinese Pharmacopoeia, 2010, Volume II.

3) The above sterile formulations were loaded into glass bottles for lyophilization to allow each bottle to contain 0.25, 0.5, 1.0, 2.0, 2.1, 4.0, 4.2, 5 or 8 mg of hepalatide.

4) The bottles for lyophilization comprising the drug formulation were placed into a freeze dryer and lyophilized according to the lyophilization method described in Example 7. After lyophilization, rubber plug was pressed and the aluminum cover was tied to form a sealed container.

Re-dissolution of the lyophilized drug formulations were detected according to the method for detecting clarity as described in Example 7.

2. Experimental Result

Figure 10:
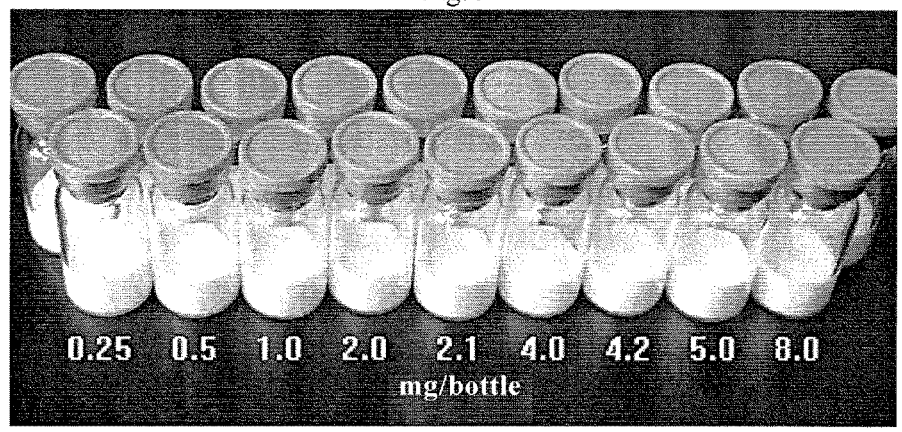
FIG. 10 shows sealed glass bottles each of which contain lyophilized formulation of hepalatide.

Sealed glass bottles containing lyophilized drug formulation were shown in FIG. 10, with each bottle containing 0.25, 0.5, 1.0, 2.0, 2.1, 4.0, 4.2, 5 or 8 mg of hepalatide, respectively. 1 ml to 5 ml injection water was respectively injected into the bottle for dissolution. All formulations could be reconstructed into liquid drug formulations and their turbidities were all less than the turbidity of No. 1 standard solution. From the subject Example, the concentration of hepalatide in the drug formulation is preferably from 0.1 mg/ml to 8.0 mg/ml, more preferably from 0.5 mg/ml to 5.0 mg/ml, more preferably from 1.0 mg/ml to 2.1 mg/ml, further more preferably from 2.0 mg/ml to 2.1 mg/ml. Preferably, the concentration of hepalatide is 0.25 mg/ml, or 0.5 mg/ml, or 1.0 mg/ml, or 2.0 mg/ml, or 2.1 mg/ml, or 4.0 mg/ml, or 4.2 mg/ml, or 5.0 mg/ml, or 10.0 mg/ml, more preferably 2.0 mg/ml or 2.1 mg/ml, and further more preferably 2.1 mg/ml. And according to this Example, each sealed container may comprise a drug formulation of hepalatide, wherein the amount of hepalatide is preferably from 0.25 mg/ml to 8.0 mg/ml, more preferably from 0.25 mg/ml to 5.0 mg/ml, more preferably from 1.0 mg/ml to 2.1 mg/ml, further more preferably from 2.0 mg/ml to 2.1 mg/ml. Each sealed container comprises a drug formulation, wherein the fixed amount of hepalatide is 0.25 mg, or 0.5 mg, or 1.0 mg, or 2.0 mg, or 2.1 mg, or 4.0 mg, or 4.2 mg, or 5.0 mg, or 8.0 mg. Preferably, each sealed container contains 0.5 mg, or 1.0 mg, or 2.0 mg, or 2.1 mg, or 4.0 mg, or 4.2 mg of hepalatide. More preferably, each sealed container contains 2.0 mg or 2.1 mg of hepalatide. Further more preferably, each sealed container contains 2.1 mg hepalatide.

EXAMPLE 25: EFFECT OF THE LYOPHILIZED DRUG FORMULATION ON IN VITRO BLOCKING HBV Infection 1. Experimental Method 1 ml to 5 ml injection water was injected into the bottles of Example 24, each of which contained a lyophilized drug formulation containing 0.25, 0.5, 1.0, 2.0, 2.1, 4.0, 4.2, 5 or 8 mg hepalatide, to reconstruct liquid drug formulations. Activity of the drug formulations on in vitro blocking HBV infection was detected according to the methods described in items 2-5 in Example 1 of CN 201010174788.X.

2. Experimental Result 1 ml injection water was injected into the bottles of Example 24, each of which contained a lyophilized drug formulation containing 0.25, 0.5, 1.0, 2.0, 2.1, 4.0, 4.2, 5 or 8 mg hepalatide, to reconstruct liquid drug formulations. The liquid drug formulations could inhibit the HBV infection of primary hepatocytes of tree shrew by 57.4%, 57.2%, 57.5%, 56.8%, 55.2%, 58.3%, 57.8%, 57.2% and 57.6%, respectively. The formulation of hepalatide that was not lyophilized inhibited HBV infection of primary hepatocytes of tree shrew by 56.9%. The PBS negative control exhibited no inhibition on in vitro HBV infection.

EXAMPLE 26: EFFECT OF THE LYOPHILIZED DRUG FORMULATION ON IN VIVO BLOCKING HBV INFECTION

1. Experimental Method 1 ml injection water was injected into the bottles of Example 24, each of which contained a lyophilized drug formulation containing 0.25, 0.5, 1.0, 2.0, 2.1, 4.0, 4.2, 5 or 8 mg hepalatide, to reconstruct liquid drug formulations. Activity of the drug formulations on in vivo blocking HBV infection was determined according to the method described in Example 4.

2. Experimental Result

As shown in Table 24, when the administration dose was 0.4 mg/kg, HbsAg and HBV DNA in serum detected 9 days after infection and ALT detected 21 days after infection could be obviously inhibited, with PBS as negative control.

TABLE 24

In vivo inhibition of HBV by lyophilized drug formulation

| Item | \multicolumn{9}{c}{Specification of formulation (mg/bottle)} | Hepalatide (not a formulation) | PBS |
|---|---|---|---|---|---|---|---|---|---|---|---|
| | 0.25 | 0.5 | 1.0 | 2.0 | 2.1 | 4.0 | 4.2 | 5 | 8 | | |
| HBsAg inhibitory rate % | 82 | 83 | 82 | 85 | 81 | 82 | 84 | 81 | 80 | 83 | 5 |
| HBV DNA inhibitory rate % | 93 | 91 | 95 | 93 | 92 | 94 | 90 | 91 | 92 | 93 | 3 |
| ALT normal rate % | 90 | 90 | 100 | 90 | 100 | 100 | 90 | 100 | 90 | 90 | 10 |

EXAMPLE 27: STUDY ON STABILITY OF THE LYOPHILIZED DRUG FORMULATION

1. Experimental Method

The stability of the lyophilized drug formulations respectively containing 0.25, 0.5, 1.0, 2.0, 2.1, 4.0, 4.2, 5.0 or 8 mg hepalatide in bottles as described in Example 24 were investigated according to the Guideline of Stability Testing of Chemical Drug. Hepalatide purity at different time points were detected according to the method described in Example 1. The re-dissolution of the lyophilized drug formulation was investigated according to the method for detected clarity as described in Example 7. Specific experiments were designed as follows.

| \multicolumn{3}{c}{Design of Accelerated Stability Test} | | |
|---|---|---|
| Test Design | Parameters | Reference |
| Temperature at which the sample was placed | 25□ ± 2□ | According to the Guideline of Stability Testing of Chemical Drug, "the accelerated test for the temperature-sensitive drug (required to be cold-stored at 4-8 □) could be carried out at 25° C. ± 2° C.". |
| Humidity at which the sample was placed | RH60% ± 5% | The sample was impermeably packaged. According to the Guideline of Stability Testing of Chemical Drug, the humidity was set to RH60% ± 5%. |
| Time point for investigation | Month 0, 1, 2, 3 6 | Guideline of Stability Testing of Chemical Drug |

| \multicolumn{3}{c}{Design for Long-term Stability Test} | | |
|---|---|---|
| Test Design | Parameters | Reference |
| Temperature at which the sample was placed | 6° C. ± 2° C. | The formulation is a polypeptide drug, which was temperature-sensitive. According to the Guideline of Stability Testing of Chemical Drug, "the long-term test for the temperature-sensitive drug can be carried out at 6° C. ± 2° C.". Thus, the temperature at which the sample was placed was set to 6° C. ± 2° C. |

| Design for Long-term Stability Test | | |
|---|---|---|
| Test Design | Parameters | Reference |
| Time point for investigation | Month 0, 3, 6, 9, 12, 18, 24 | Guideline of Stability Testing of Chemical Drug |

2. Experimental Result

At each time point for investigation, each lyophilized formulation was dissolved by injectable water. It was found that their turbidities were all less than that of No. 1 turbidity standard solution, indicating that they satisfied the related requirements on injection prescribed in Chinese Pharmacopoeia. As shown in Table 25, the lyophilized drug formulation in a specification of from 0.25 mg/bottle to 8 mg/bottle were stable in the 6-month accelerated stability test and were also stable over 24 months in the long-term stability test. They could fully satisfy the formulation production, transport, storage and clinical use.

TABLE 25

| Purity (%) of hepalatide in lyophilized drug formulations detected by HPLC at different time points | | | | | | | | | |
|---|---|---|---|---|---|---|---|---|---|
| Time | Specification of Formulation (mg/bottle) | | | | | | | | |
| (month) | 0.25 | 0.5 | 1.0 | 2.0 | 2.1 | 4.0 | 4.2 | 5.0 | 8.0 |
| Accelerated Stability | | | | | | | | | |
| 0 | 99.4 | 99.3 | 99.4 | 99.4 | 99.4 | 99.4 | 99.4 | 99.4 | 99.4 |
| 1 | 99.3 | 99.4 | 99.4 | 99.4 | 99.3 | 99.3 | 99.4 | 99.4 | 99.1 |
| 2 | 99.4 | 99.4 | 99.3 | 99.4 | 99.4 | 99.4 | 99.4 | 99.4 | 99.4 |
| 3 | 99.4 | 99.3 | 99.4 | 99.4 | 99.4 | 99.3 | 99.4 | 99.4 | 99.2 |
| 6 | 99.1 | 99.3 | 99.3 | 99.3 | 99.3 | 99.3 | 99.3 | 99.4 | 99.4 |

TABLE 25-continued

| Purity (%) of hepalatide in lyophilized drug formulations detected by HPLC at different time points | | | | | | | | | |
|---|---|---|---|---|---|---|---|---|---|
| Time | Specification of Formulation (mg/bottle) | | | | | | | | |
| (month) | 0.25 | 0.5 | 1.0 | 2.0 | 2.1 | 4.0 | 4.2 | 5.0 | 8.0 |
| Long-term Stability | | | | | | | | | |
| 0 | 99.4 | 99.4 | 99.4 | 99.4 | 99.4 | 99.4 | 99.4 | 99.4 | 99.4 |
| 3 | 99.3 | 99.3 | 99.4 | 99.1 | 99.4 | 99.4 | 99.0 | 99.4 | 99.4 |
| 6 | 99.4 | 99.4 | 99.3 | 99.4 | 99.3 | 99.3 | 99.4 | 99.4 | 99.5 |
| 9 | 99.42 | 99.4 | 99.4 | 99.4 | 99.4 | 99.4 | 99.1 | 99.4 | 99.4 |
| 12 | 99.4 | 99.2 | 99.3 | 99.3 | 99.2 | 99.4 | 99.4 | 99.4 | 99.1 |
| 18 | 99.3 | 99.4 | 99.4 | 99.4 | 99.4 | 99.4 | 99.4 | 99.4 | 99.2 |
| 24 | 99.4 | 99.4 | 99.3 | 99.4 | 99.4 | 99.4 | 99.3 | 99.4 | 99.4 |

The above specific Examples are merely for illustrative purpose but not for limiting purpose. The protection scope of the subject application shall be defined by the claims. The skilled artisan will understand that any modification and change could be made to the technical solution of the present disclosure without departing from the spirit and scope of the present disclosure. All these modifications and changes still fall within the scope of the present disclosure.

SEQUENCE LISTING STATEMENT

The application includes the sequence listing that is concurrently filed in computer readable form. This sequence listing is incorporated by reference herein.

What is claimed is:

1. A formulation comprising (i) a polypeptide having an amino acid sequence set forth in SEQ ID NO:1; (ii) a buffer salt; (iii) an osmotic regulator; and (iv) an excipient;

wherein the drug formulation is formulated in water, the N terminus of the polypeptide is modified by myristic acid and the C terminus is modified by amidation; and wherein the osmotic regulator is NaCl, the excipient is mannitol and the concentration of the polypeptide is in a range of 0.25-8.0 mg/ml, and NaCl is in a molar concentration of 116~154 mM and mannitol is in a concentration (W/V) of 1~5%; or the osmotic regulator is glucose, the excipient is mannitol, dextran or sorbitol, and the concentration of the polypeptide is in a range of 0.25-1.0 mg/ml, wherein the concentration of glucose is 5% (W/V), and the concentration of mannitol, dextran or sorbitol is 4% (W/V).

2. The drug formulation of claim 1, wherein the buffer salt is a phosphate buffer salt or a carbonate buffer salt.

3. The drug formulation of claim 2, wherein the molar concentration of phosphate radical in the phosphate buffer salt is:
   (a) 0.001~0.50 M,
   (b) 0.01~0.10 M,
   (c) 0.02~0.05 M, or
   (d) 0.02 M.

4. The drug formulation of claim 2, wherein in the phosphate buffer salt the molar ratio between $Na_2HPO_4$:$NaH_2PO_4$ is:
   (a) 0:100~100:0,
   (b) 70:30~95:5,
   (c) 81:19~95:5, or
   (d) 90:10.

5. The drug formulation of claim 1, wherein the osmotic regulator is in a molar concentration of:
   116 mM.

6. The drug formulation of claim 1, wherein the excipient is mannitol in a concentration (W/V) of:
   4%.

7. The drug formulation of claim 1, wherein the molar concentration of phosphate radical in the phosphate buffer salt is 0.02 M, and the molar ratio between $Na_2HPO_4$:$NaH_2PO_4$ in the phosphate buffer salt is 90:10.

8. The drug formulation of claim 1, wherein the buffer salt is phosphate buffer salt, the osmotic regulator is NaCl and the excipient is mannitol, and the molar concentration of phosphate radical in the phosphate buffer salt is 0.02 M, the molar ratio between $Na_2HPO_4$:$NaH_2PO_4$ in the phosphate buffer salt is 90:10, the molar concentration of NaCl is 116 mM, and the concentration (W/V) of mannitol is 4%.

9. The drug formulation of claim 1, wherein the polypeptide is present in an amount of:
   (a) 0.25~5.0 mg/ml, or
   (b) 1.0~2.1 mg/ml.

10. The drug formulation of claim 1, wherein the polypeptide is present in an amount of 0.25 mg/ml, or 0.5 mg/ml, or 1.0 mg/ml, or 2.0 mg/ml, or 2.1 mg/ml, or 4.0 mg/ml, or 4.2 mg/ml, or 5.0 mg/ml, or 8.0 mg/ml.

11. The drug formulation of claim 1, wherein the drug formulation is selected from the group of drug formulations consisting of the following formulation:
   (a) polypeptide 8.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 8.0 g, mannitol 40 g, $Na_2HPO_4.12H_2O$ 6.4465 g, $NaH_2PO_4.2H_2O$ 0.3120 g, NaCl 6.7744 g;
   (b) polypeptide 5.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 5.0 g, mannitol 40 g, $Na_2HPO_4.12H_2O$ 6.4465 g, $NaH_2PO_4.2H_2O$ 0.3120 g, NaCl 6.7744 g;
   (c) polypeptide 4.2 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 4.2 g, mannitol 40 g, $Na_2HPO_4.12H_2O$ 6.4465 g, $NaH_2PO_4.2H_2O$ 0.3120 g, NaCl 6.7744 g;
   (d) polypeptide 4.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 4.0 g, mannitol 40 g, $Na_2HPO_4.12H_2O$ 6.4465 g, $NaH_2PO_4.2H_2O$ 0.3120 g, NaCl 6.7744 g;
   (e) polypeptide 2.1 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 2.1 g, mannitol 40 g, $Na_2HPO_4.12H_2O$ 6.4465 g, $NaH_2PO_4.2H_2O$ 0.3120 g, NaCl 6.7744 g;
   (f) polypeptide 2.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 2.0 g, mannitol 40 g, $Na_2HPO_4.12H_2O$ 6.4465 g, $NaH_2PO_4.2H_2O$ 0.3120 g, NaCl 6.7744 g;
   (g) polypeptide 1.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 1.0 g, mannitol 40 g, $Na_2HPO_4.12H_2O$ 6.4465 g, $NaH_2PO_4.2H_2O$ 0.3120 g, NaCl 6.7744 g;
   (h) polypeptide 0.5 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 0.5 g, mannitol 40 g, $Na_2HPO_4.12H_2O$ 6.4465 g, $NaH_2PO_4.2H_2O$ 0.3120 g, NaCl 6.7744 g; and
   (i) polypeptide 0.25 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 0.25 g, mannitol 40 g, $Na_2HPO_4.12H_2O$ 6.4465 g, $NaH_2PO_4.2H_2O$ 0.3120 g, NaCl 6.7744 g.

12. The drug formulation of claim 1 which is sterilized and/or lyophilized.

13. A packaging drug product comprising in a sealable container the drug formulation of claim 1.

14. A packaging drug product of claim 13, wherein in the drug formulation, the buffer salt is phosphate buffer salt, the osmotic regulator is NaCl and the excipient is mannitol, and the polypeptide is present in an amount of:
(a) 0.25~5.0 mg/ml, or
(b) 1.0~2.1 mg/ml;
the molar concentration of phosphate radical in the phosphate buffer salt is:
(a) 0.001~0.50 M,
(b) 0.01~0.10 M,
(c) 0.02~0.05 M, or
(d) 0.02 M;
in the phosphate buffer salt the molar ratio between $Na_2HPO_4:NaH_2PO_4$ is:
(a) 0:100~100:0,
(b) 70:30~95:5,
(c) 81:19~95:5, or
(d) 90:10;
NaCl is in a molar concentration of:
(a) 116~154 mM, or
(b) 116 mM; and
mannitol is in a concentration (W/V) of:
(a) 1~5%, or
(b) 4%.

15. A liquid drug formulation prepared from re-dissolution of a lyophilized drug formulation of claim 1 with injectable water.

16. The liquid drug formulation of claim 15, wherein in the drug formulation, the buffer salt is phosphate buffer salt, the osmotic regulator is NaCl and the excipient is mannitol, and
the polypeptide is present in an amount of:
(a) 0.25~5.0 mg/ml, or
(b) 1.0~2.1 mg/ml;
the molar concentration of phosphate radical in the phosphate buffer salt is:
(a) 0.001~0.50 M,
(b) 0.01~0.10 M,
(c) 0.02~0.05 M, or
(d) 0.02 M;
in the phosphate buffer salt the molar ratio between $Na_2HPO_4:NaH_2PO_4$ is:
(a) 0:100~100:0,
(b) 70:30~95:5,
(c) 81:19~95:5, or
(d) 90:10;
NaCl is in a molar concentration of:
(a) 116~154 mM, or
(b) 116 mM; and
mannitol is in a concentration (W/V) of:
(a) 1~5%, or
(b) 4%.

17. The liquid drug formulation of claim 9, wherein in the drug formulation, the buffer salt is phosphate buffer salt, the osmotic regulator is NaCl and the excipient is mannitol, and
the polypeptide is present in an amount of
(a) 0.25~5.0 mg/ml, or (b) 1.0~2.1 mg/ml;
the molar concentration of phosphate radical in the phosphate buffer salt is:
(a) 0.001~0.50 M,
(b) 0.01~0.10 M,
(c) 0.02~0.05 M, or
(d) 0.02 M;
in the phosphate buffer salt the molar ratio between $Na_2HPO_4:NaH_2PO_4$ is:
(a) 0:100~100:0,
(b) 70:30~95:5,
(c) 81:19~95:5, or
(d) 90:10;
NaCl is in a molar concentration of:
(a) 116~154 mM, or
(b) 116 mM; and
mannitol is in a concentration (W/V) of:
(a) 1~5%, or
(b) 4%.

18. The packaging drug product of claim 13, wherein the drug formulation is selected from the group of drug formulations consisting of the following formulation:
(a) polypeptide 8.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 8.0 g, mannitol 40 g, $Na_2HPO_4.12H_2O$ 6.4465 g, $NaH_2PO_4.2H_2O$ 0.3120 g, NaCl 6.7744 g;
(b) polypeptide 5.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 5.0 g, mannitol 40 g, $Na_2HPO_4.12H_2O$ 6.4465 g, $NaH_2PO_4.2H_2O$ 0.3120 g, NaCl 6.7744 g;
(c) polypeptide 4.2 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 4.2 g, mannitol 40 g, $Na_2HPO_4.12H_2O$ 6.4465 g, $NaH_2PO_4.2H_2O$ 0.3120 g, NaCl 6.7744 g;
(d) polypeptide 4.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 4.0 g, mannitol 40 g, $Na_2HPO_4.12H_2O$ 6.4465 g, $NaH_2PO_4.2H_2O$ 0.3120 g, NaCl 6.7744 g;
(e) polypeptide 2.1 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 2.1 g, mannitol 40 g, $Na_2HPO_4.12H_2O$ 6.4465 g, $NaH_2PO_4.2H_2O$ 0.3120 g, NaCl 6.7744 g;
(f) polypeptide 2.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 2.0 g, mannitol 40 g, $Na_2HPO_4.12H_2O$ 6.4465 g, $NaH_2PO_4.2H_2O$ 0.3120 g, NaCl 6.7744 g;
(g) polypeptide 1.0 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 1.0 g, mannitol 40 g, $Na_2HPO_4.12H_2O$ 6.4465 g, $NaH_2PO_4.2H_2O$ 0.3120 g, NaCl 6.7744 g;
(h) polypeptide 0.5 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 0.5 g, mannitol 40 g, $Na_2HPO_4.12H_2O$ 6.4465 g, $NaH_2PO_4.2H_2O$ 0.3120 g, NaCl 6.7744 g; and
(i) polypeptide 0.25 mg/ml, mannitol 4% (w/v), $Na_2HPO_4$ 18 mM, $NaH_2PO_4$ 2 mM, and NaCl 116 mM, when calculated in 1000 ml liquid formulation, the 1000 ml liquid formulation comprises polypeptide 0.25 g, mannitol 40 g, $Na_2HPO_4 \cdot 12H_2O$ 6.4465 g, $NaH_2PO_4 \cdot 2H_2O$ 0.3120 g, NaCl 6.7744 g.

* * * * *